United States Patent
Bain et al.

(12) 
(10) Patent No.: US 6,551,330 B1
(45) Date of Patent: Apr. 22, 2003

(54) LINEAR SUTURING APPARATUS AND METHODS

(75) Inventors: Gregory H. Bain, Laguna Niguel, CA (US); Seth Foerster, San Clemente, CA (US)

(73) Assignee: Opus Medical, Inc., San Juan Capistrano, CA (US)

( * ) Notice: Subject to any disclaimer, the term of this patent is extended or adjusted under 35 U.S.C. 154(b) by 243 days.

(21) Appl. No.: 09/668,055

(22) Filed: Sep. 21, 2000

(51) Int. Cl.[7] ............................................. A61B 17/04
(52) U.S. Cl. ....................................................... 606/144
(58) Field of Search ................................. 606/139, 144, 606/148

(56) References Cited

U.S. PATENT DOCUMENTS

| | | |
|---|---|---|
| 2,269,963 A | 1/1942 | Wappler |
| 3,946,740 A | 3/1976 | Bassett |
| 4,109,658 A | 8/1978 | Hughes |
| 4,164,225 A | 8/1979 | Johnston et al. |
| 4,345,601 A | 8/1982 | Fukuda |
| 4,493,323 A | 1/1985 | Albright et al. |
| 4,621,640 A | 11/1986 | Mulhollan et al. |
| 4,635,637 A | 1/1987 | Schreiber |
| 4,738,255 A | 4/1988 | Goble et al. |
| 4,741,330 A | 5/1988 | Hayhurst |
| 4,836,205 A | 6/1989 | Barrett |
| 4,923,461 A | 5/1990 | Caspari et al. |
| 4,926,860 A | 5/1990 | Stice et al. |
| 4,935,027 A | 6/1990 | Yoon |
| 4,957,498 A | 9/1990 | Caspari et al. |
| 4,981,149 A | 1/1991 | Yoon et al. |
| 5,037,422 A | 8/1991 | Hayhurst et al. |
| 5,046,513 A | 9/1991 | Gatturna et al. |
| 5,059,201 A * | 10/1991 | Asnis .......................... 606/139 |
| 5,085,661 A | 2/1992 | Moss |
| 5,304,184 A | 4/1994 | Hathaway et al. |
| 5,417,699 A | 5/1995 | Klein et al. |
| 5,431,666 A * | 7/1995 | Sauer et al. ................. 606/139 |
| 5,445,167 A | 8/1995 | Yoon et al. |
| 5,527,322 A | 6/1996 | Klein et al. |
| 5,609,597 A | 3/1997 | Lehrer |
| 5,613,974 A | 3/1997 | Andreas et al. |
| 5,645,552 A | 7/1997 | Sherts |
| 5,665,108 A | 9/1997 | Galindo |
| 5,741,281 A | 4/1998 | Martin |
| 5,776,150 A | 7/1998 | Nolan et al. |
| 5,779,719 A | 7/1998 | Klein et al. |

(List continued on next page.)

FOREIGN PATENT DOCUMENTS

| | | | |
|---|---|---|---|
| EP | 0535906 A2 | * | 4/1993 |
| WO | WO 91/06247 | * | 5/1991 |

Primary Examiner—John J. Calvert
Assistant Examiner—Shaun R Hurley
(74) Attorney, Agent, or Firm—Stout, Uxa, Buyan & Mullins, LLP; Donald E. Stout

(57) ABSTRACT

A suturing instrument and methods for placing mattress stitches in soft tissues comprises an elongate shaft with a stationary jaw and a movable jaw disposed at a distal end thereof. The movable jaw is coupled to a handle grip at the proximal end of the shaft and is configured to manipulate the movable jaw into open and closed positions respective to the stationary jaw. The jaws are configured to permit atraumatic grasping of soft tissues to be sutured. The stationary jaw is comprised of a serrated face, incorporating apertures through which needles may be driven distally into and through the grasped tissue and into needle capture cans attached to opposing ends of a single strand of suture material. The serrated upper jaw is configured with capture means adapted to accept and capture the needles and suture. The handle is released to open the movable jaw, after which the instrument may be withdrawn, trailing the suture, and leaving a mattress stitch in the grasped tissue.

32 Claims, 32 Drawing Sheets

U.S. PATENT DOCUMENTS

| | | | |
|---|---|---|---|
| 5,792,152 A | | 8/1998 | Klein et al. |
| 5,792,153 A | * | 8/1998 | Swain et al. ................ 112/169 |
| 5,860,991 A | | 1/1999 | Klein et al. |
| 5,860,992 A | * | 1/1999 | Daniel et al. ............... 606/139 |
| 5,902,311 A | | 5/1999 | Andreas et al. |
| 5,921,994 A | | 7/1999 | Andreas et al. |
| 5,947,982 A | * | 9/1999 | Duran ........................ 606/139 |
| 5,984,933 A | | 11/1999 | Yoon |
| 6,001,109 A | | 12/1999 | Kontos |
| 6,036,699 A | | 3/2000 | Andreas et al. |
| 6,048,351 A | | 4/2000 | Gordon et al. |
| 6,096,051 A | * | 8/2000 | Kortenbach et al. ........ 606/144 |

* cited by examiner

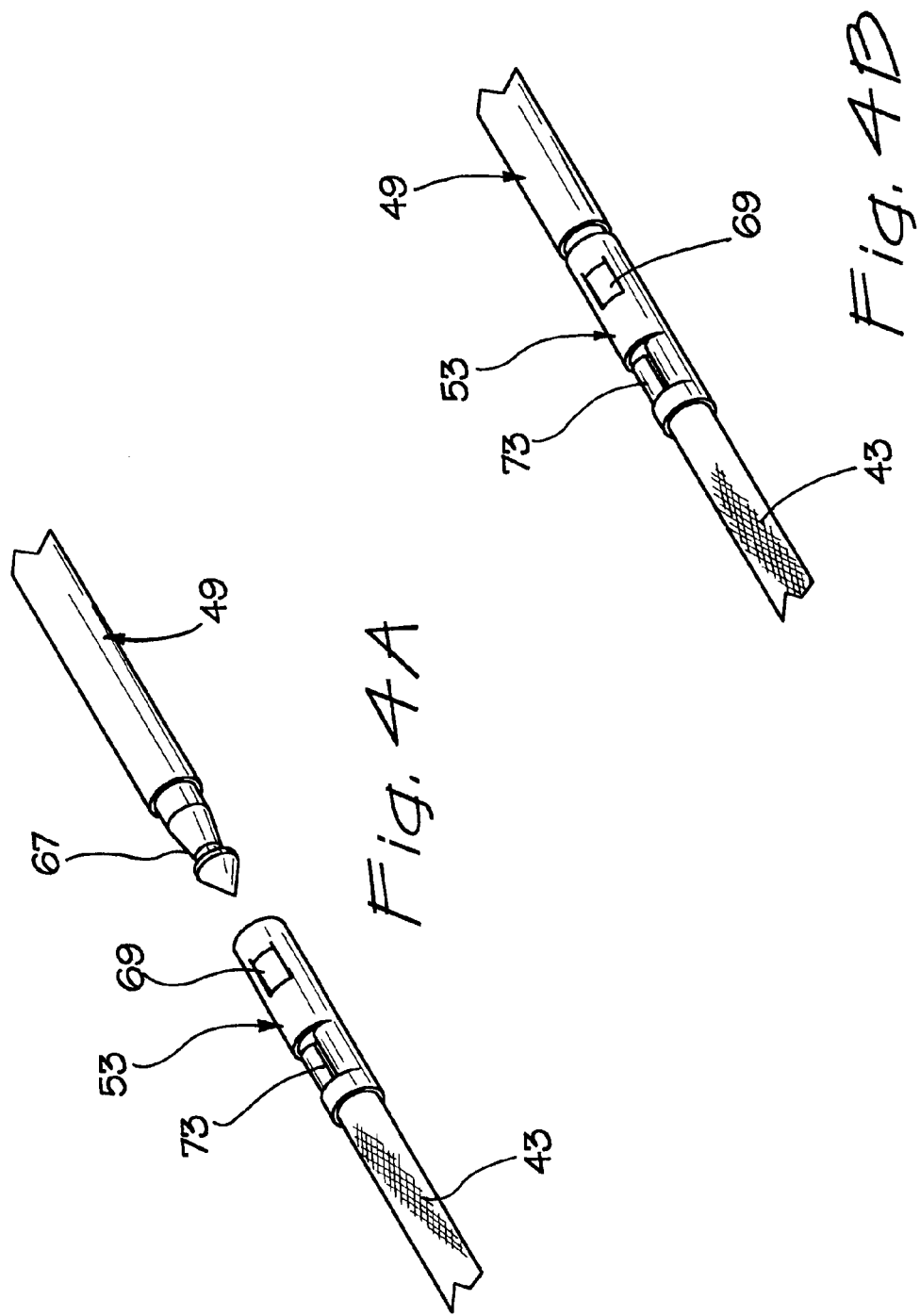

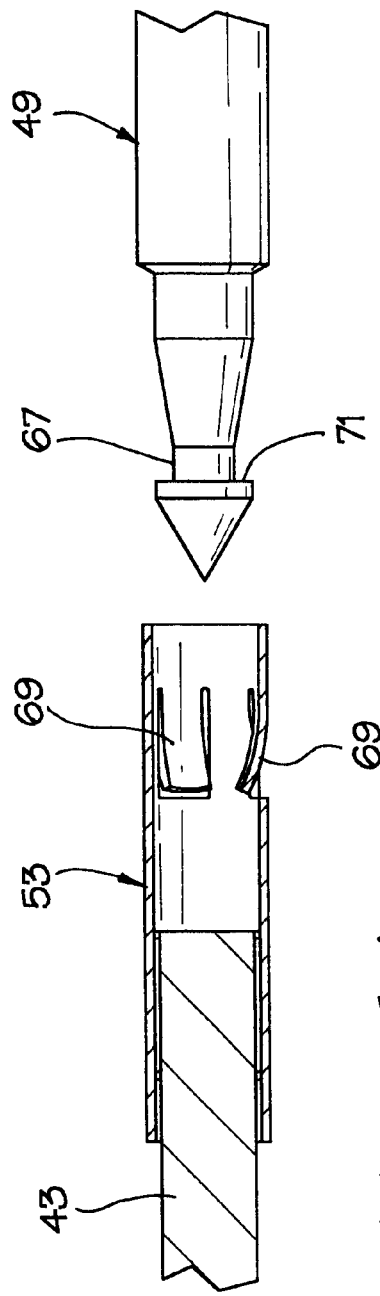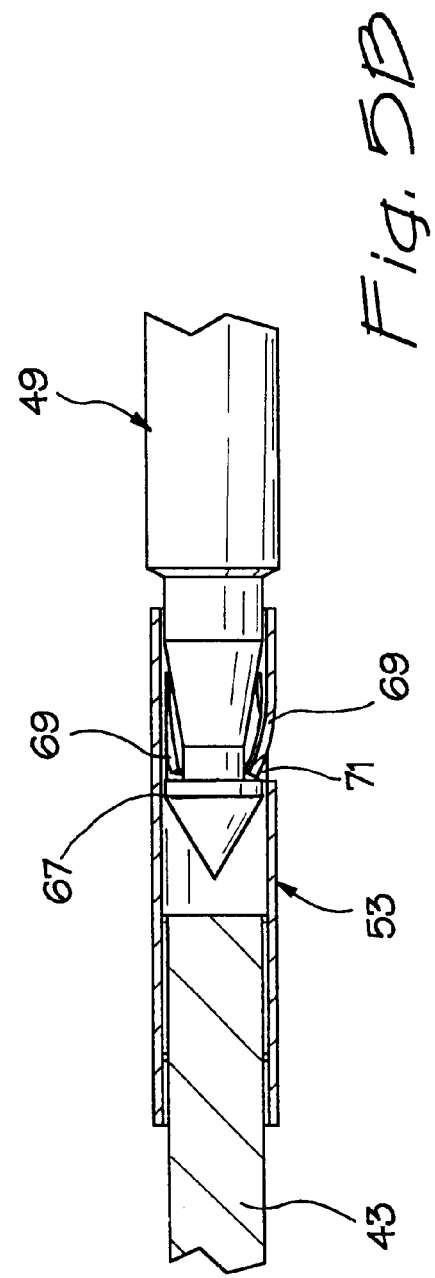

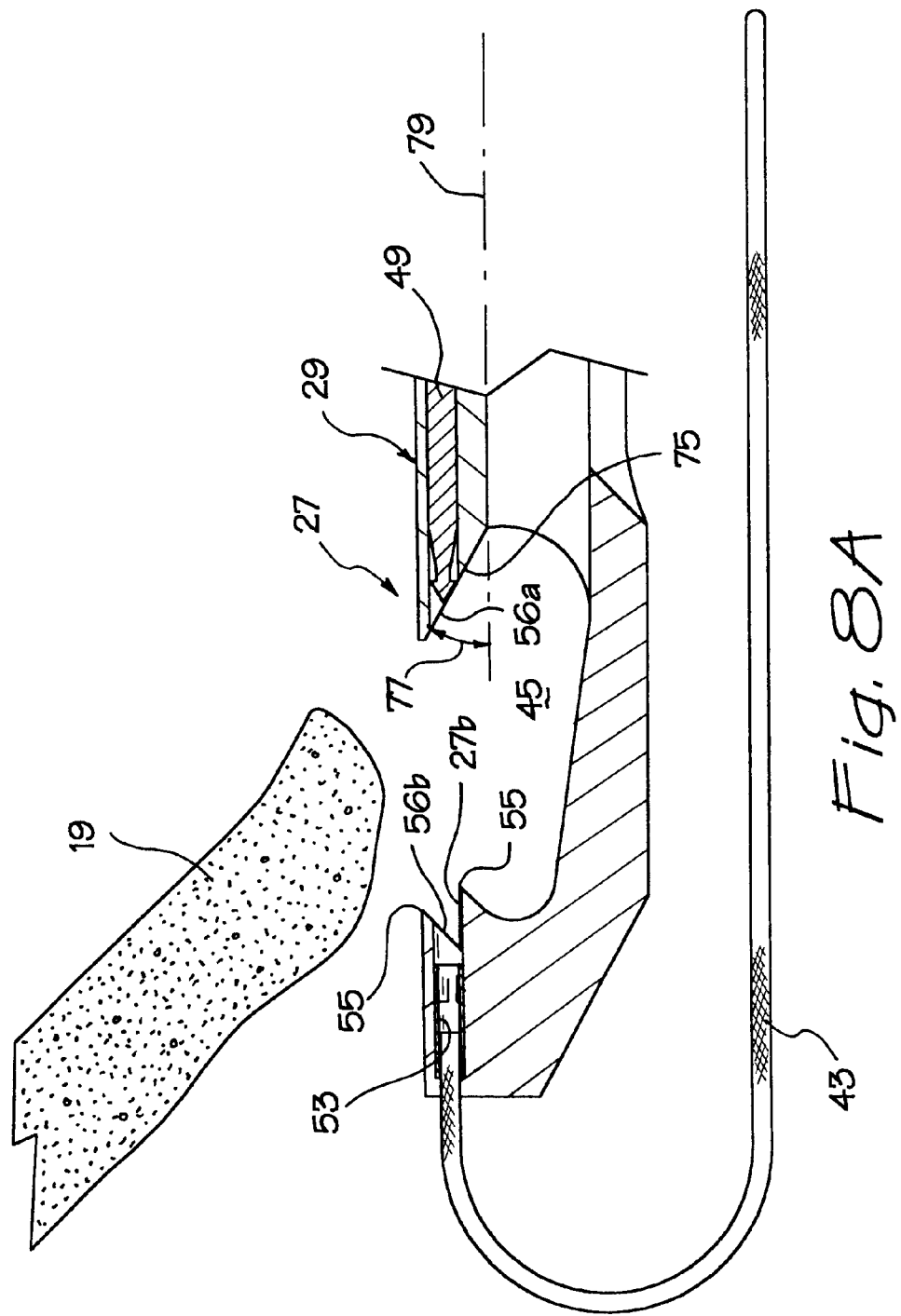

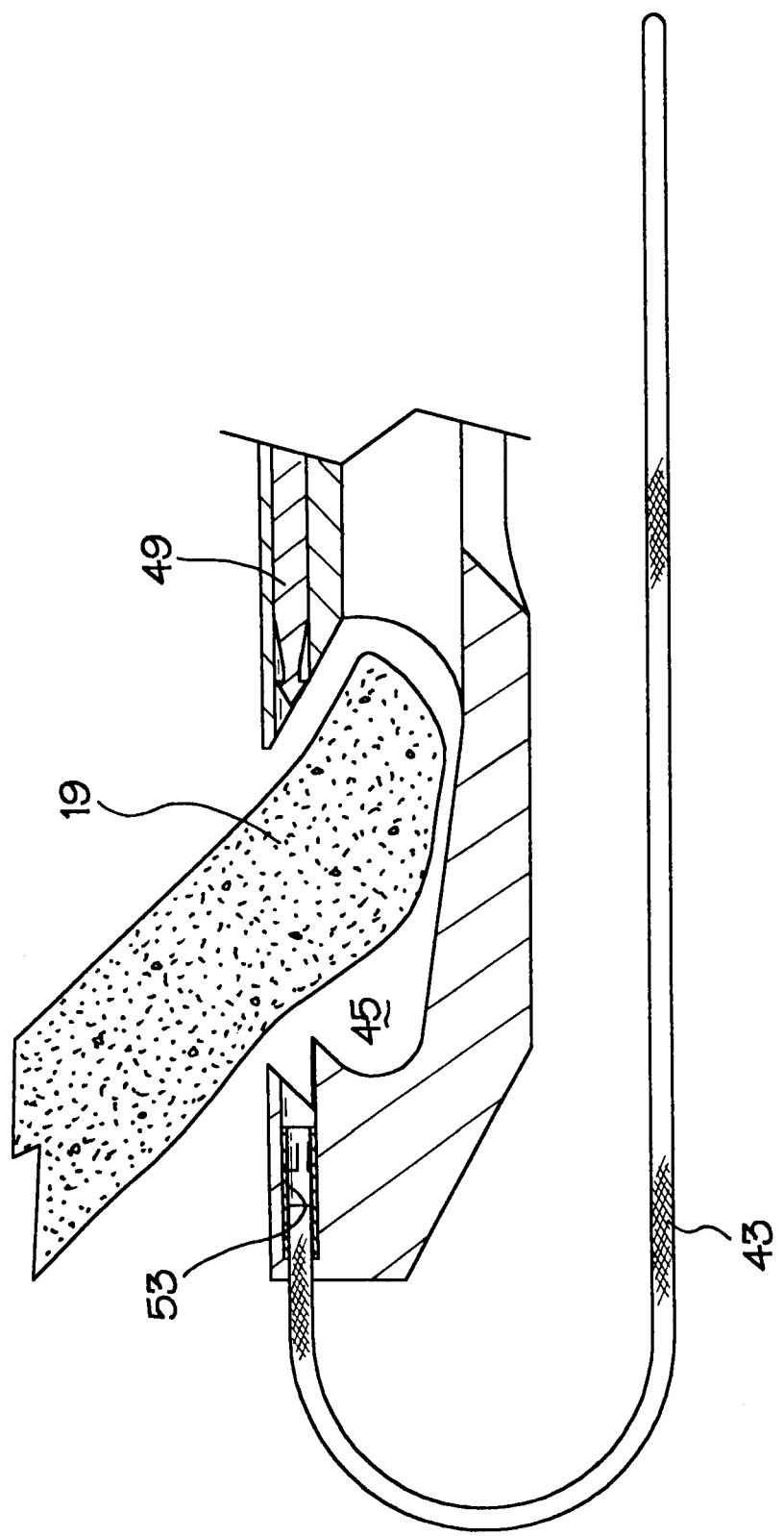

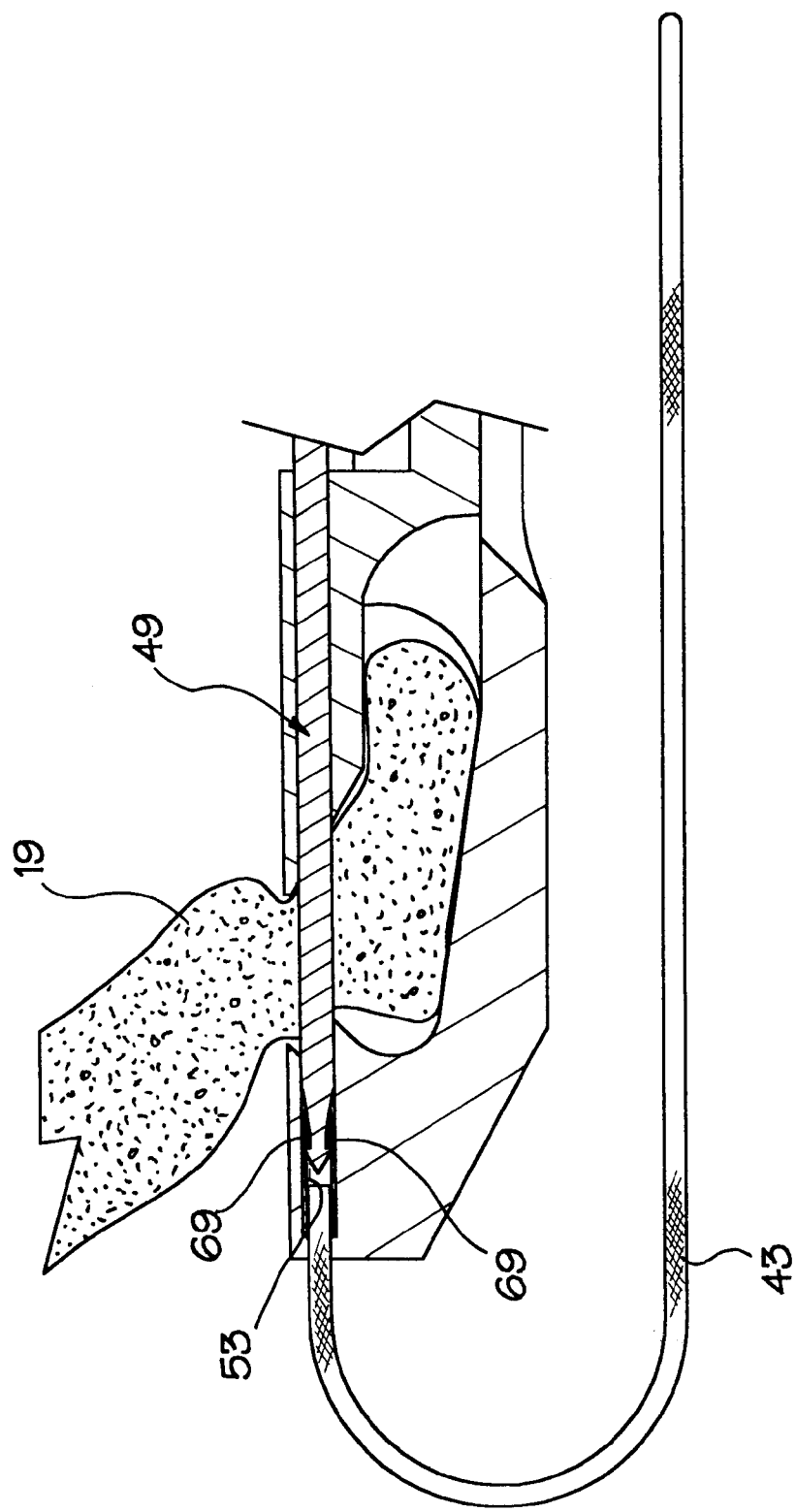

LINEAR SUTURING APPARATUS AND METHODS

This application is related to co-pending application Ser. No. 09/475,495, filed on Dec. 30, 1999, and entitled Method and Apparatus for Attaching Connective Tissues to Bone Using a Knotless Suture Anchoring Device, and co-pending application Ser. No. 09/547,171, filed on Apr. 11, 2000, and entitled Dual Function Suturing Apparatus and Method, both of which are herein expressly incorporated by reference.

BACKGROUND OF THE INVENTION

The present invention relates to a method and apparatus for placing sutures in tissue, and more particularly to a method and device for arthroscopic repair of a torn rotator cuff.

Suturing of body tissues is a time consuming aspect of most surgical procedures. Many surgical procedures are currently being performed where it is necessary to make a large opening to expose an area of the body which requires surgical repair. There are instruments that are becoming increasingly available that allow the viewing of certain areas of the body through a small incision without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle-carrying suture through body tissues to approximate, ligate and fixate them. Many prior disclosures, such as described in U.S. Pat. No. 919,138 to Drake et al, employ a hollow needle driven through the tissue with the suture material passing through the hollow center lumen of the needle. The needle is withdrawn, leaving the suture material in place, and the suture is tied, completing the approximation. A limitation of these types of devices is that they are particularly adapted for use in open surgical procedures, involving a large incision, where there is room for the surgeon to manipulate the instrument.

Others have attempted to devise suturing instruments that resemble traditional forceps, such as U.S. Pat. No. 3,946,740 to Bassett. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope becomes the surgeons' substitute eyes by which they operate. Operations using an endoscope are significantly less invasive when compared to traditional open surgery. Patients usually return home the next day or in some cases, the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes.

Such an instrument is disclosed in U.S. Pat. No. 4,621,640 to Mulhollan et al. The Mulhollan et al. patent describes an instrument that may be used to hold and drive a needle, but makes no provision for retrieval of the needle from the body cavity, nor the completion of the suture by tying. Mulhollan's instrument is limited in that the arc through which the needle must be driven is perpendicular to the axis of the device.

Another such instrument intended for endoscopic use is described by U.S. Pat. No. 4,935,027 to Yoon. This instrument uses oppositional hollow needles or tracks pushed through the tissue and coapted to create a tract through which the suture material is pushed. It is not clear how the curved tracks would be adapted to both be able to pierce the tissue planes illustrated, parallel to the tips of the tracks, and be curved toward each other to form the hollow tract.

Yet another instrument and method is shown by Caspari in U.S. Pat. Nos. 4,923,461 and 4,957,498. Caspari discloses an endoscopic instrument suitable for use through a trocar that resembles the Yoon approach, but with a single hollow needle on one of a set of oppositional jaws. The jaws simultaneously close, grasping the tissue. The jaw opposite the hollow needle has a window through which the hollow needle passes as the jaws close, freeing the lumen of the hollow needle from the tissue. Much like Yoon, a suture or suture snare is pushed down through the lumen and retrieved from the suture site, the jaws are released, and the suture is pulled back out through the trocar. This device may be used to place simple stitches in tissues that have been mobilized and have an edge accessible to the jaws. A limitation of the device is the manipulation that must be done with the snare if a suture other than a monofilament is used.

Another instrument specifically adapted for the orthopedic surgeon for the repair of a torn anterior cruciate ligament or for meniscal repair is disclosed by U.S. Pat. No. 4,836,205 to Barrett. The Barrett patent combines in a single instrument the functions of grasping the tissue to be sutured and the passing of the needles through that tissue. It is to be understood that this instrument is designed for use specifically under endoscopic view, and through trocars as previously described. A fairly generic endoscopic grasper is disclosed that has been adapted to allow for a hollow lumen from the handle of the grasper down to the distal tip of the grasper jaws. An elongate needle of 8 to 10 inches in length may be passed through this hollow lumen. The needle, being significantly longer than the grasper, is introduced through the handle of the grasper, and may be driven through the tissue being held in the grasping jaws of the device. The needle is then retrieved from the tissue via a trocar port placed substantially opposite the port through which the grasper is introduced. If a mattress stitch is desired, two needles attached to opposite ends of a suture are both passed through the tissue and retrieved. A limitation of this device is that there must be both visual and physical access to both sides of the tissue flap to be sutured. This requires trocars to be placed opposite each other and roughly on a line intercepting the tissue. This is a severe limitation in the instance of shoulder repair, and specifically in repair of the rotator cuff.

There have been other attempts to improve the methods of tissue repair. These include the development of staplers and anchoring devices. In response to some of the aforementioned problems in placing sutures in tissues endoscopically, manufacturers have developed tissue staplers. These devices utilize stainless steel or titanium staples that are constructed much like the staples used to hold papers together. The major disadvantage of these kinds of staplers is that they leave metal in the body. For some tissues this is not a problem, however in some procedures, metal staples left within the tissues can be a major hindrance to the healing process.

In orthopedic surgery, many different designs for bone anchors have been developed. These anchors allow soft tissues to be reattached to bone, and simplify the process by removing the need to create a trans-osseous tunnel. Trans-osseous tunnels are created in bones to allow suture material to be threaded through and tied across the bony bridge created by tunnels after it has been placed through the soft tissues and tied with conventional knots. Anchors fabricated from stainless steel or titanium are commonly used in joint reconstructions, and, because the metal is contained in the bone, it does not cause a problem with healing.

While endoscopy has certainly found favor with many physicians as an alternative operative modality, the advanced skill set and operative time necessary to become an efficient and practiced endoscopist have proven to be a challenge for a large portion of the surgical community. The cost pressures brought about by large scale patient management (the continued rise and success of health maintenance organizations or HMO's) have also caused the surgical community to cast a critical eye on the overall costs and long-term outcomes of some of the procedures that have been tried via an endoscopic approach. While the laparoscopic cholecystectomy (gall bladder removal) has certainly proven its worth in the past 8–10 years, many other procedures have not shown similar cost effectiveness and positive long-term outcomes.

Hence, alternatives have been sought to bridge the gap between the preferred endoscopic surgery, which is skill and equipment intensive, and the more familiar and easier open surgery, which is much more invasive and results in greater long-term discomfort and recovery time on the part of the patient. As such, under the broad umbrella of "minimally invasive surgery" which would include endoscopic surgery, a relatively new approach called "mini-incision surgery" has begun to emerge. This approach uses the principles of traditional open surgery, along with some of the equipment advances of endoscopy to provide the patient with the best of both worlds.

Perhaps the most visible of these new approaches is the emergence of minimally invasive heart surgery, both for coronary bypass and for valve replacement. Techniques and tools for cardiovascular surgery have begun to be used that allow the heart surgeon to perform procedures through small incisions between the ribs that previously required a massive incision and splitting the sternum to gain access to the heart.

In a similar way, orthopedic surgeons have begun to explore alternatives to the traditional open approach for the many indications requiring reconstruction of some aspect of the shoulder. As they did in adopting minimally invasive approaches to knee repair and re-construction, the use of either an endoscopic or a "mini-open" approach is gaining in popularity with surgeons, patients and third party payers.

It is an increasingly common problem for tendons and other soft, connective tissues to tear or to detach from associated bone. One such type of tear or detachment is a "rotator cuff" tear, causing pain and loss of ability to elevate and externally rotate the arm. Complete separation can occur if the shoulder is subjected to gross trauma, but typically, the tear begins as a small lesion, especially in older patients.

The rotator cuff or a shoulder joint is made up of a combination of the distal tendinous portion of four muscles, supraspinatus and subspinatus, subscapularis and teres minor. The cuff is attached to the upper, anterior and posterior faces of the trochiter by covering the upper pole of the humeral head. Proper functioning of the tendinous cuff, 3 to 4 millimeters thick, depends on the fundamental centering and stabilizing role of the humeral head with respect to sliding action during anterior and lateral lifting and rotational movements of the arm.

The musculotendinous cuff passes under an osteofibrous arch, which is made up from the front to the rear by a portion of the acromion, the coracoacromial ligament and the coracoid process, thereby forming a canal. A sliding bursa passes between the musculotendinous cuff and the walls of the osteofibrous arch. Therefore, there is a potential and sometimes detrimental interaction between the musculotendinous cuff and the acromiocoracoidian arch, particularly during lateral and anterior lifting movements of the arm. The repeated rubbing of the cuff against the walls of the osteofibrous arch results in the wearing of the tendinous cuff by progressive abrasion. The rubbing can be increased inasmuch as arthrosis lesions with severe osteophytes may thicken the walls of the aforementioned arch, becoming more aggressive as the cuff gets older.

With time, gradual thinning is brought about, accompanied by a trophic perforation (less than 1 $cm^2$) of the cuff, particularly in the hypo-vascularized and fragile area where the supraspinatus muscle is joined. A fall may provide a more extensive rupture by disjunction of the supraspinatus muscle, with extension towards the front (subscapularis muscle) or the rear (subspinatus muscle). The degenerative rupture of the rotator or musculotendinous cuff may be of a varied size:

grade 1—perforation (less than 1 $cm^2$) reaching the supraspinatus muscle;

grade 2—supraspinatus-rupture (greater than 1 $cm^2$);

grade 3—massive rupture concerning the supraspinatus, subspinatus, subscapularis muscles and sometimes the teres minor muscle.

It is possible to carry out surgery to reconstruct the rotator cuff. This is done by re-covering the humeral head, giving back to the cuff its capturing and stabilizing role and re-establishing a harmonious scapulohumeral rhythm. Reconstruction requires excision of the coracoacromial ligament and cleaning the subacromial space, including suppression of the arthrosis legions and thinning of the anterior portion of the acromion.

The typical course for repair of a torn rotator cuff today is to do so through an open incision. This approach is presently taken in almost 99% of rotator cuff repair cases. Two types of open surgical approaches are known for repair of the rotator cuff, one of which is known as the "classic open" and the other as the "mini-open". The "classic open" approach typically requires a large incision of 6 to 9 centimeters (cm) and complete detachment of the deltoid muscle from the acromion to facilitate exposure. Following the suturing of the rotator cuff to the humeral head, the detached deltoid is surgically reattached. Because of this maneuver, the deltoid requires postoperative protection, thus retarding rehabilitation and possibly resulting in residual weakness. Complete rehabilitation takes approximately 9 to 12 months.

The "mini-open" technique, which represents the current growing trend and the majority of all surgical repair procedures, differs from the classic approach by gaining access through a smaller incision of 3 to 5 cm and splitting rather than detaching the deltoid. Additionally, this procedure is typically used in conjunction with arthroscopic acromial decompression. Once the deltoid is split, it is retracted to expose the rotator cuff tear. The cuff is debrided and trimmed to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as trans-osseous tunnels, are "punched" through the bone laterally from the abraded or notched surface to a point on the outside surface of the greater tuberosity, commonly a distance of 2 to 3 cm.

There are a few different methods for placing the suture material in the supraspinatus tendon. Because one of the most common failure modes for rotator cuff repair lies in the sutures pulling out of the soft tissue, much care is taken to place the sutures such that the most security possible is achieved. This is typically done by using a either a mattress stitch or a more complex stitch called a "modified Mason-Allen". The goal of both of these stitches is to spread the forces imparted by the sutures on the tissues by involving a pledget of tissue between the entry and exit points of the suture ends. The mattress stitch incorporates essentially a down, over and back up path for the suture.

Finally, the cuff is secured to the bone by pulling the suture ends through the trans-osseous tunnels and tying them together using the bone between two successive tunnels as a bridge, after which the deltoid muscle must be surgically reattached to the acromion.

Although the above described surgical technique is the current standard of care for rotator cuff repair, it is associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally using instruments and techniques such as the Caspari punch previously described. This creates a simple stitch instead of the more desirable mattress or Mason-Allen stitch. Rather than threading the suture through trans-osseous tunnels which are difficult or impossible to create arthroscopically using current techniques, an anchor is driven into bone at a location appropriate for repair. The repair is completed by tying the cuff down against bone using the anchor and suture.

Early results of less invasive techniques are encouraging, with a substantial reduction in both patient recovery time and discomfort. However, as mentioned supra, this approach places only one loop of suture in the cuff for each anchor, reducing the fundamental strength of the repair. The knots in the tendon can be bulky and create a painful impingement of the tendon on the bone. This is because the knots end up on top of the cuff, in the sub-acromial space, and have a tendency to rub on the acromion as the arm is raised. Because non-absorbable suture materials are used for these types of repairs, the suture and associated knots are not absorbed into the body, and hence provide a constant, painful reminder of their presence.

None of the prior art devices are adaptable to effect the placement of a mattress stitch in grasped tissues, nor are they adaptable to place sutures precisely and controllably while making provision for needle retrieval when using endoscopic techniques. None of the prior art devices make it possible to place a mattress stitch into, for example, the supraspinatus tendon utilizing an endoscopic approach.

What is needed, therefore, is a family of novel suturing devices that overcome the above described disadvantages of prior known devices in a simple and economical manner. The devices should be capable of arthroscopically creating a mattress stitch in a tendon to increase the soft tissue pullout strength of the repaired tendon. They should also be capable of suturing the tendon or other soft tissue without requiring traditional knots to secure the suture to the tendon.

SUMMARY OF THE INVENTION

Accordingly, the inventors have developed a new and novel approach for securing a mattress stitch in a tissue flap. An instrument that combines the function of both grasping the tissue and passing sutures through the tissue to form a mattress stitch is herein described. The instrument includes a pair of grasping jaws that oppose each other along a line parallel to the long axis of the instrument. The distal end of the instrument incorporates the fixed jaw, and proximal to that jaw is a moveable jaw that is controlled by the user via an actuator, such as a lever, on the hand grip.

Advantageously, the present invention provides a family of novel suturing devices that overcome the above described disadvantages of known prior art devices in a simple and economic manner. The inventive system creates a mattress stitch in the damaged tendon to be repaired which increases the soft tissue pullout strength substantially over prior art approaches, yet does not require the traditional knots to secure the suture to the tendon.

In a preferred method of the present invention, the instrument is inserted through a portal known as a trocar cannula. The portal is created by first making an incision in the skin, and then inserting a cannula through the incision to the repair site. The distal end of the instrument inserted through the cannula is under direct visualization from a second trocar cannula that has been previously inserted, using a visualization instrument, such as an endoscope, inserted through the second trocar cannula. The instrument is inserted until the jaws reach, for example, torn rotator cuff tissue. In operation, the distal end of the grasper aspect of the instrument is positioned at the repair site beneath the tissue to be grasped. The movable jaw slides toward the stationary jaw responsive to actuation of the aforementioned lever actuator, which is preferably disposed in a handle. The handle lever moves inwardly to actuate the jaw by pivoting about a pivot pin. Once the appropriate section of tissue is isolated and grasped by the jaws, the lever may be locked in its closed position using a latch mechanism.

Once the practitioner is satisfied with the placement of the grasper on the grasped tissue, he or she can then deploy the suture needles to create a mattress stitch in the tissues to be repaired (a torn rotator cuff, for example). In operation, the suture needles may be advanced through the grasped tissues by pushing on a button or other suitable actuation means. The button actuator is directly connected to the needles via a connecting rod, and the button is pushed against the force of a return spring. In turn, the connecting rod pushes a needle carriage, wherein suture needles are held in the carriage. The needle carriage resides behind the proximal movable jaw of the instrument, and responsive to the actuation of the button via the connecting rod described supra, is able to move distally to cause the needles to pass through the movable jaw. As the carriage continues to move distally, the tips of the suture needles begin to clear the distal edge of apertures created in the proximal movable jaw and then begin to penetrate through the top of the grasped tissue and to advance distally towards the stationary jaw.

The stationary jaw incorporates two apertures that are adapted to receive the ends of the suture. Each suture has been crimped into a small piece of hypodermic tubing that has been configured to have a set of tabs, preferably about three or four, which are fabricated into the periphery of the tube and bent inwardly toward the central axis of the tube at an acute angle. As the suture needles approach the end of their stroke, the distal end of the needles have passed completely through the grasped tissues and begin to enter the apertures in the stationary distal jaw. As previously mentioned, those apertures are configured to accept the suture ends that have been attached to the modified hypodermic tubing.

At this point, any pull force being applied by the grasper on the grasped tissues is relaxed. Once the tissue is in a relaxed state, the jaws of the grasper are then opened. The handle lever is unlocked from the locking mechanism, and returns to an open position due to the pull force exerted on it by means of a return spring. As the return spring pulls on the lever, it pivots about a pin.

To complete the pull out of the suture needles, it is necessary to pull on the grasper and to remove it from the repair site. The instrument can be retracted back through the portal via the trocar cannula. As the instrument is removed from the suture site, the free ends of the suture are removed as well. This causes the suture to pass through the tissues at the puncture sites. As the suture is pulled through, the loop end of the suture is pulled snug against the underside of the tissues to form what is referred to as a mattress stitch. This process may be repeated as necessary, depending upon the number of sutures required for the particular procedure being undertaken.

Advantageously, as will be apparent to those skilled in the art, the implementation in one compact instrument of the combined function of grasping tissues to be sutured and precisely placing a mattress stitch in the grasped sutures, while working through a trocar port, is a significant advance in the art. The inventive instrument also permits the reloading of additional sutures and suture needles for the placement of subsequent stitches.

More particularly, there is provided a suturing device for use endoscopically, which comprises a first jaw member and a second jaw member, both of which are disposed at a distal end of the suturing device. An actuator, preferably comprising a handpiece, is disposed at a proximal end of the suturing device, for actuating the first and second jaw members between a closed orientation, wherein the first and second jaw members are disposed in close proximity to one another, and an open orientation, wherein the first and second jaw members are substantially spaced from one another. A hollow barrel is disposed between the actuator and the first and second jaw members. A linking member within the hollow barrel connects the actuator with the first jaw member; and Additionally, at least one needle is disposed at the distal end of the suturing device, and is movable between a retracted position and an extended position for passage through tissue grasped between the first and second jaw members.

Advantageously, the first jaw member is axially movable relative to the second jaw member, to thereby move the jaw members between the aforementioned closed and open orientations.

In preferred embodiments, the handpiece actuator comprises a handle grip and a handle lever, with the handle lever being movable relative to the handle grip. More particularly, the handle lever is pivotally mounted relative to the handle grip, such that it is pivotable between a first position corresponding to the closed orientation of the first and second jaw members and a second position corresponding to the open orientation of the first and second jaw members. A latching mechanism, such as a ratcheting system having complementary engaging teeth, is provided for securing the handle lever relative to the handle grip, to thereby also secure the first and second jaw members in a desired orientation.

Importantly, at least one needle (and preferably two spaced needles) is disposed on a needle carriage, which is axially movable between distal and proximal positions at the distal end of the suturing device. A second actuator, preferably comprising a knob actuator (though, of course, many different types of actuation mechanisms may be employed) is disposed at the proximal end of the suturing device, for actuating the needle carriage to move axially between its distal and proximal positions. In preferred embodiments, a spring is provided for biasing the needle carriage in its proximal position.

A recess is provided in the distal end of the suturing device, for receiving portions of the tissue, such as a torn rotator cuff, which is to be grasped between the first and second jaw members. In preferred embodiments, the first jaw member slides axially across an opening of the recess when the first and second jaw members move between the open orientation and the closed orientation.

In another aspect of the invention, there is provided a suturing device for use endoscopically, which comprises a first jaw member and a second jaw member. The first and second jaw members are disposed at a distal end of the suturing device and are movable between a closed orientation, wherein the first and second jaw members are in close proximity to one another, and an open orientation, wherein the first and second jaw members are substantially spaced from one another. A needle carriage is provided, which is axially movable between distal and proximal positions at the distal end of the suturing device. At least one needle (and preferably two spaced needles) is disposed on the needle carriage, the axial movement of the needle carriage functioning to move the at least one needle between a retracted position and an extended position, for passage through tissue grasped between the first and second jaw members.

In preferred embodiments, an actuator is disposed at a proximal end of the suturing device, for actuating the first and second jaw members between the aforementioned closed and open orientations. Preferably, only one of the first and second jaw members moves when the actuator actuates the jaw members between the closed and the open orientations, however.

In yet another aspect of the invention, there is provided a suturing device for use endoscopically, which comprises a first jaw member and a second jaw member, wherein the first and second jaw members are disposed at a distal end of the suturing device. An actuator is disposed at a proximal end of the suturing device, for actuating the first and second jaw members between a closed orientation, wherein the first and second jaw members are disposed in close proximity to one another, and an open orientation, wherein the first and second jaw members are substantially spaced from one another. At least one, and preferably two spaced needles are disposed on the distal end of the suturing device, wherein each needle includes a penetrating tip and is movable between a retracted position and an extended position for passage through tissue grasped between the first and second jaw members. The spaced needles are oriented so that the penetrating tip of each needle moves distally relative to the suturing device when the needle is moved from the retracted position to the extended position.

In still another aspect of the invention, there is provided a suturing device which comprises a first jaw member and a second jaw member. The first and second jaw members are disposed at a distal end of the suturing device, and are movable between a closed orientation, wherein the first and second jaw members are disposed in close proximity to one another, and an open orientation, wherein the first and second jaw members are substantially spaced from one another. At least one needle is disposed at the distal end of the suturing device, which is movable between a retracted position and an extended position for passage through tissue grasped between the first and second jaw members. Preferably, the at least one needle moves axially between the retracted and extended positions, and distally when moving from the retracted position to the extended position.

Apertures are disposed in each of the first and second jaw members, through which the at least one needle passes when moving between the retracted and extended positions. The at least one needle is then received into at least one corresponding can when the at least one needle moves from the retracted position to the extended position. The at least one can is disposed on an end of a length of suturing material.

In preferred configurations, the at least one can is disposed in the second jaw member, which is distal to the first jaw member, and remains stationary relative to the first jaw member when the jaw members are moved between their closed and open orientations. The at least one can comprises a plurality of tabs for preventing separation of the at least one needle from the at least one can, once the at least one needle has been received by the at least one can. The number of needles corresponds to the number of cans, which is preferably two in both instances (i.e. two needles and two corresponding cans).

In another aspect of the invention, there is disclosed a method of placing sutures in tissue, using a suturing device which comprises first and second jaw members which are disposed at a distal end of the suturing device and at least one needle which is also disposed at the suturing device distal end, wherein at least one needle is movable from a retracted position to an extended position. The method comprises steps of inserting the distal end of the suturing device through a trocar port until the first and second jaw members are adjacent to tissue which is to be repaired, and then actuating the first and second jaw members to close together, thus capturing the tissue therebetween (between the two jaw members). Then the at least one needle is actuated to move from the retracted position to the extended position, so that the at least one needle extends through the captured tissue. As it becomes fully extended through the captured tissue, the at least one needle is received in at least one can, wherein each of the at least one cans is attached to a corresponding length of suturing material.

Additional preferred steps of the method may comprise, for example, a step of retracting the at least one needle proximally through the captured tissue, wherein the proximal travel of the at least one needle also causes the at least one can and attached length of suturing material to travel proximally through the captured tissue, thereby creating a stitch through the tissue. This stitch is preferably a "mattress stitch". Then, the suturing instrument is withdrawn proximally through the trocar port. In preferred embodiments, the at least one needle comprises a spaced pair of needles, and the at least one can comprises a corresponding pair of cans, each of which is secured to an end of a corresponding length of suturing material.

The invention, together with additional features and advantages thereof, may best be understood by reference to the following description taken in conjunction with the accompanying illustrative drawing.

BRIEF DESCRIPTION OF THE DRAWINGS

FIGS. 3A through 3G are schematic cross-sectional views of a distal tissue clamping portion of the instrument shown in FIGS. 2A through 2E, illustrating in sequence the tissue clamping aspect of the procedure illustrated in FIGS. 2A through 2E;

FIGS. 4A and 4B are perspective sequential views illustrating the needle coupling mechanism of the inventive instrument;

FIGS. 5A and 5B are cross-sectional sequential views of the needle coupling mechanism shown in FIGS. 4A and 4B;

FIGS. 8A through 8G are schematic sequential cross-sectional views similar to FIGS. 3A through 3G, but showing an enlarged view of the tissue clamping portion of the instrument;

DESCRIPTION OF THE PREFERRED EMBODIMENT

The present invention relates to a method and apparatus for the arthroscopic repair of torn tissue and bone at a surgical repair site using a device, which is a combination tissue grasper and suture placement device. Although the present invention is described primarily in conjunction with the repair of a torn rotator cuff, the apparatus and method could also be used in arthroscopic repair at other sites, such as the knee, elbow, or hip, for example, as well as in conjunction with other surgical techniques, such as traditional open or mini-open surgical procedures.

Figure 1:
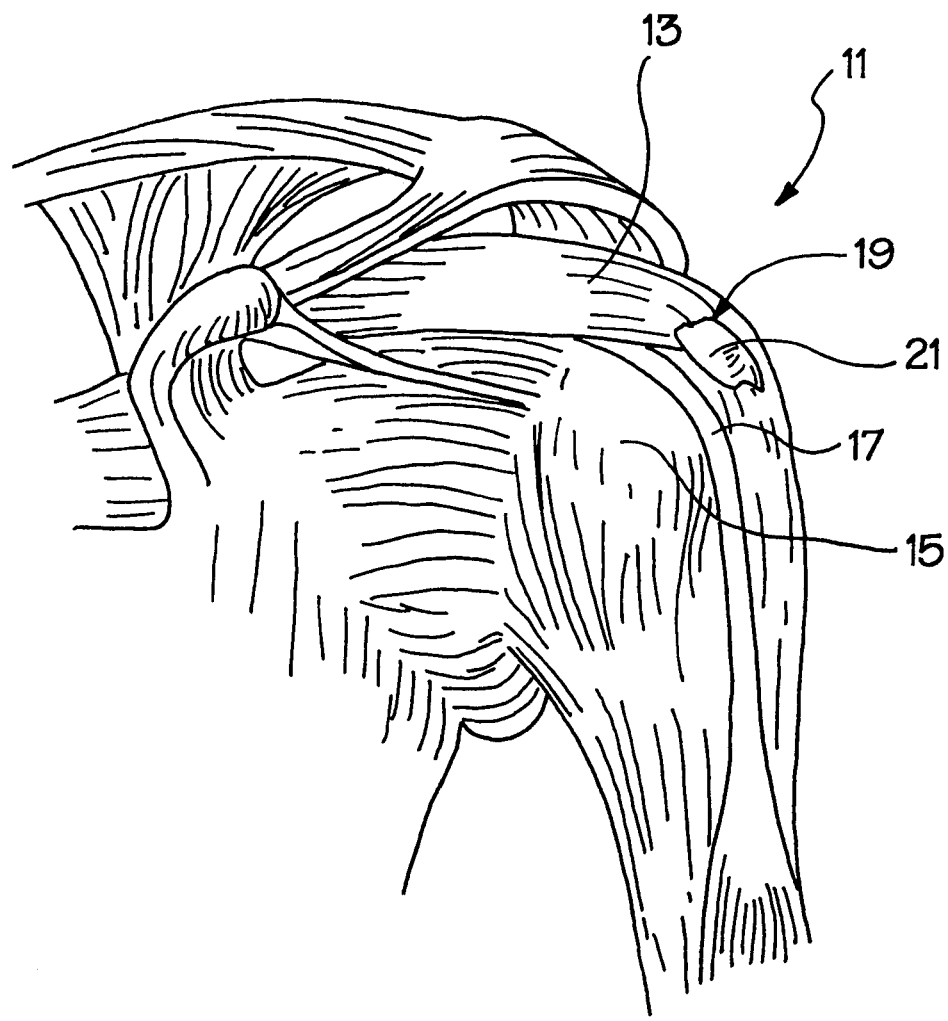
FIG. 1 is a diagram of a typical shoulder joint, illustrating a torn rotator cuff.

Referring now to FIG. 1, there is shown representative shoulder musculature 11, including a supraspinatus muscle 13, a deltoid muscle 15, a biceps tendon 17, a torn rotator cuff 19, and a humeral head 21. The humeral head 21 is not normally visible, as it is typically covered by the rotator cuff 19. However, in the illustration, the torn rotator cuff 19 has pulled away from the head 21 of the humerus, exposing it to view.

Referring now more particularly to FIGS. 2A through 2E, there is illustrated the general structure and function of an embodiment constructed and operated in accordance with the principles of the present invention. A trocar port 23 has been inserted into the shoulder joint, providing a conduit through which a linear suturing device 25 may be passed. The linear suturing device 25 is provided with movable jaws 27 for grasping portions of the torn rotator cuff 19. The jaws 27 are disposed at a distal end 29 of a hollow barrel 31. A handpiece 33 is disposed at a proximal end 35 of the hollow barrel 31, and is adapted to actuate the movable jaws 27. In the present preferred embodiment, the handpiece 33 comprises a handle grip 37 and a handle lever 39, which pivots about a pivot pin 41. In a manner to be fully described below, the handle lever 39 is suitably connected to the jaws 27 to actuate the jaws between an open and a closed position, depending upon the position of the handle lever 39, relative to the handle grip 37. Of course, the actuating mechanism which is illustrated for moving the jaws 27 between their open and closed positions, through presently preferred, is only exemplary. Many other types of similar actuating mechanisms are known to those skilled in the art, and any of those would be suitable for the present application.

Figure 2A:
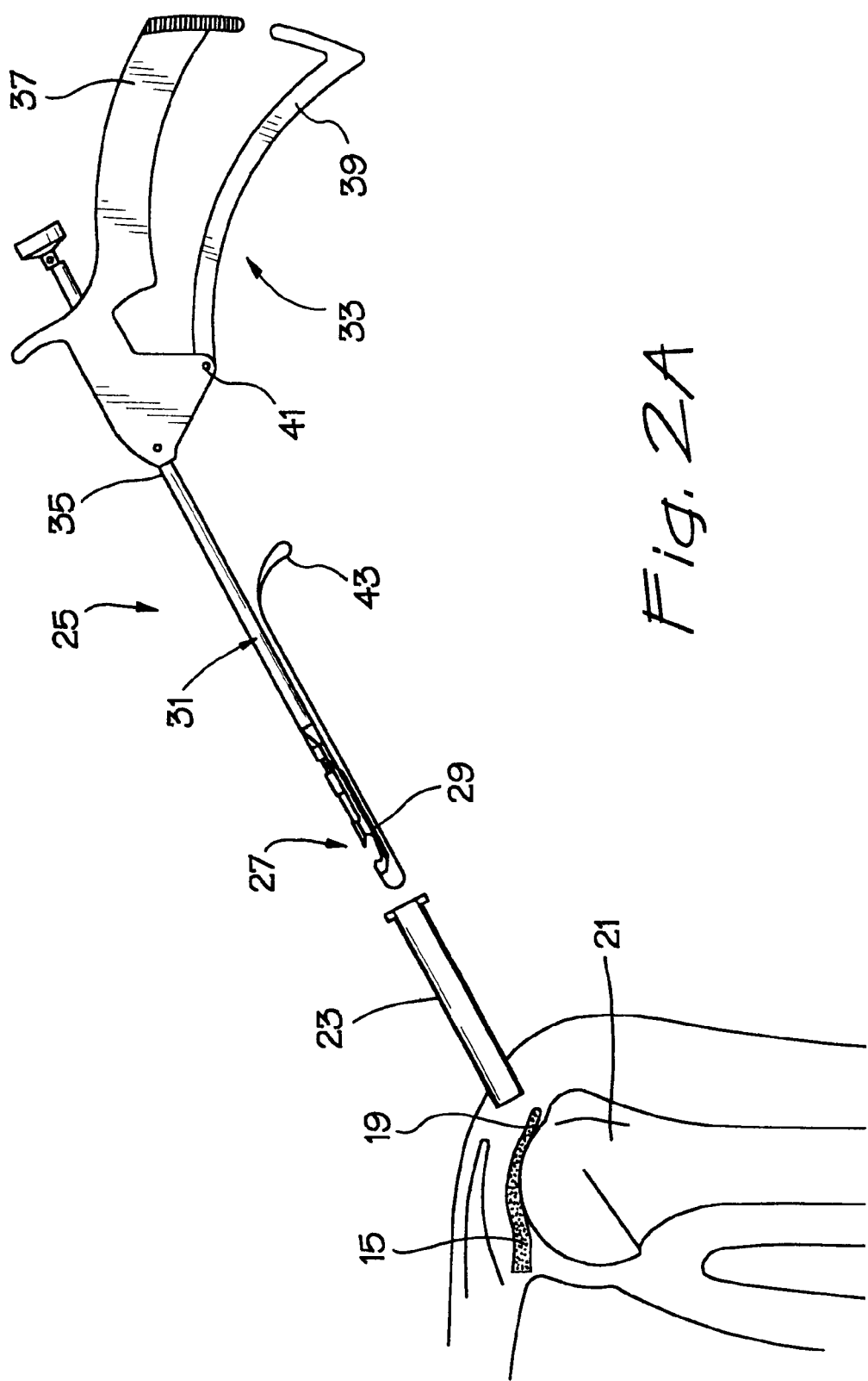
FIGS. 2A through 2E are schematic plan views illustrating one embodiment of the invention, and a preferred method, in sequence, for using same.

In FIG. 2A, the suturing device 25 is shown with the jaws 27 open, trailing a suture 43, ready to be placed into the shoulder joint through the trocar port 23, which was previously created by first making an incision in the skin, and then inserting a cannula through the incision to the procedural site, in a manner known in the art.

Figure 2B:
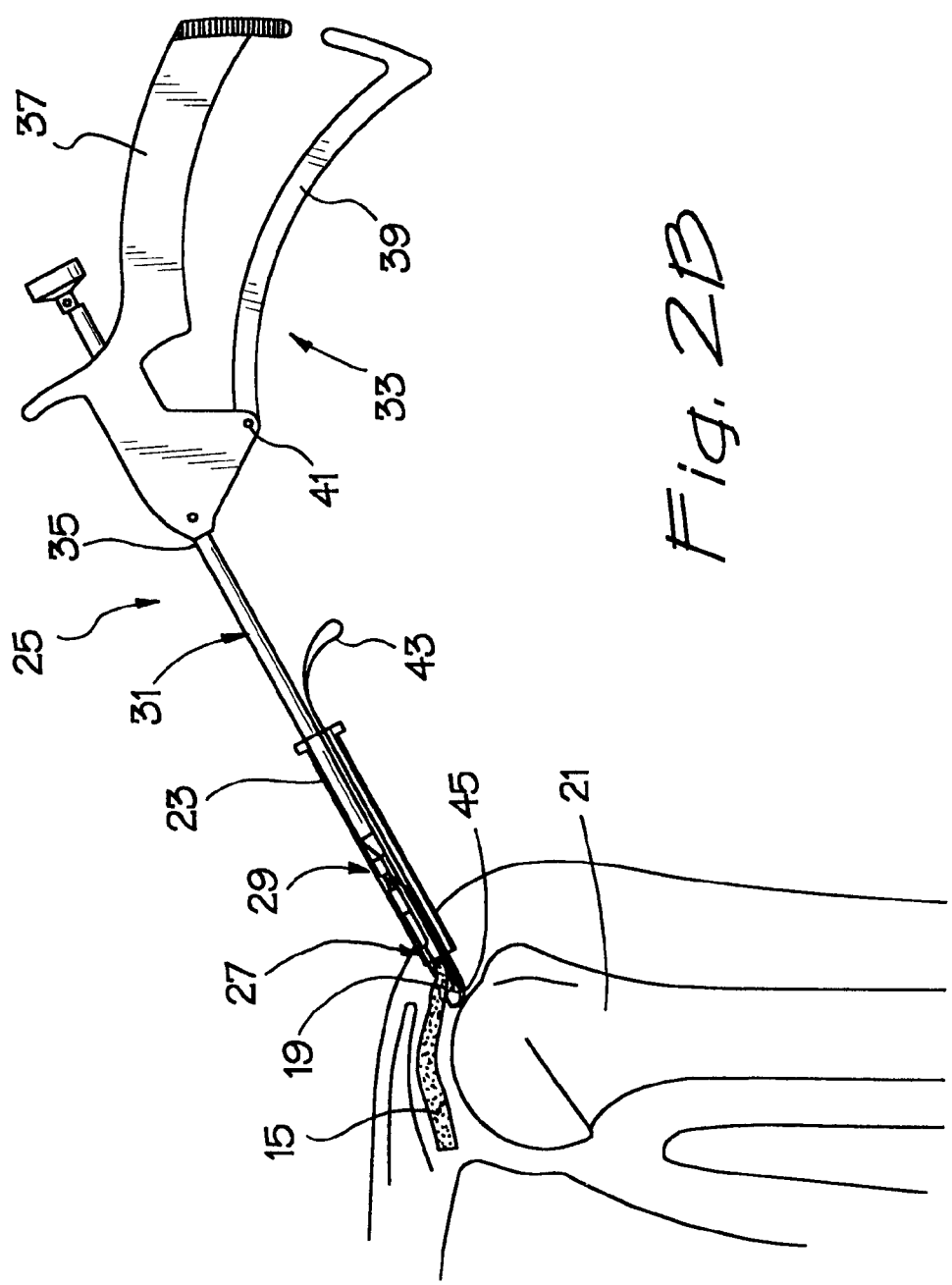

FIG. 2B illustrates the suturing device 25 having been inserted through the trocar port 23 into the shoulder joint, with the jaws 27 remaining in an opened position. The jaws 27 are oriented such that a portion of the torn rotator cuff 19 is situated in a recess 45 within the distal end 29 of the suturing device 25. Visualization of the procedural site is obtained by means of an endoscope or the like, which is inserted into a position in proximity to the procedural site through a second trocar cannula, not shown.

Figure 2C:
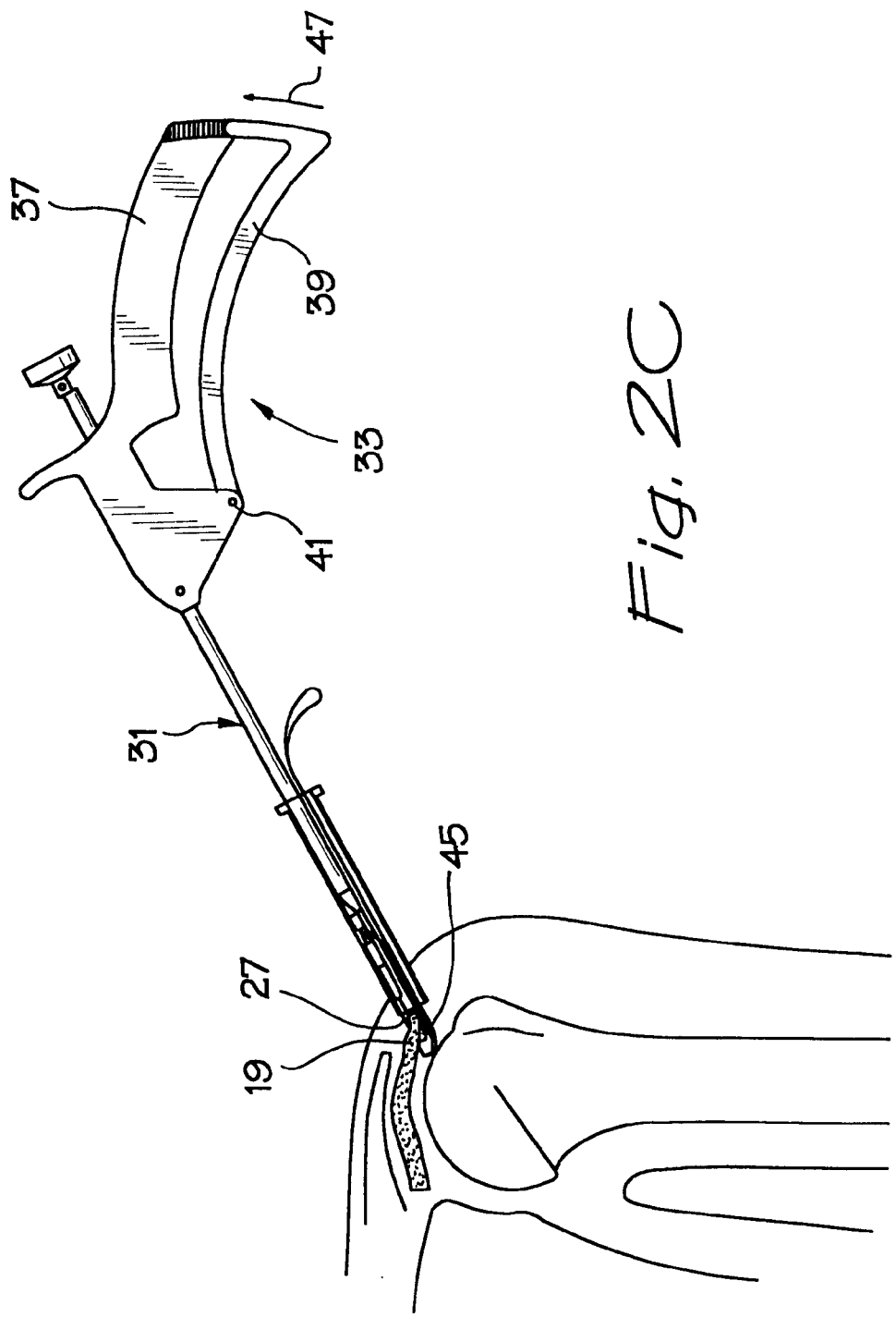

As shown in FIG. 2C, the handle lever 39 is actuated by squeezing it toward the handle grip 37, in a direction shown by arrow 47. As the lever 39 travels toward the grip 37, it pivots about the pin 41. This lever action causes the jaws 27 to move distally, as illustrated, thereby grasping the tissues of the torn rotator cuff 19 which are disposed within the recess 45.

Figure 2D:
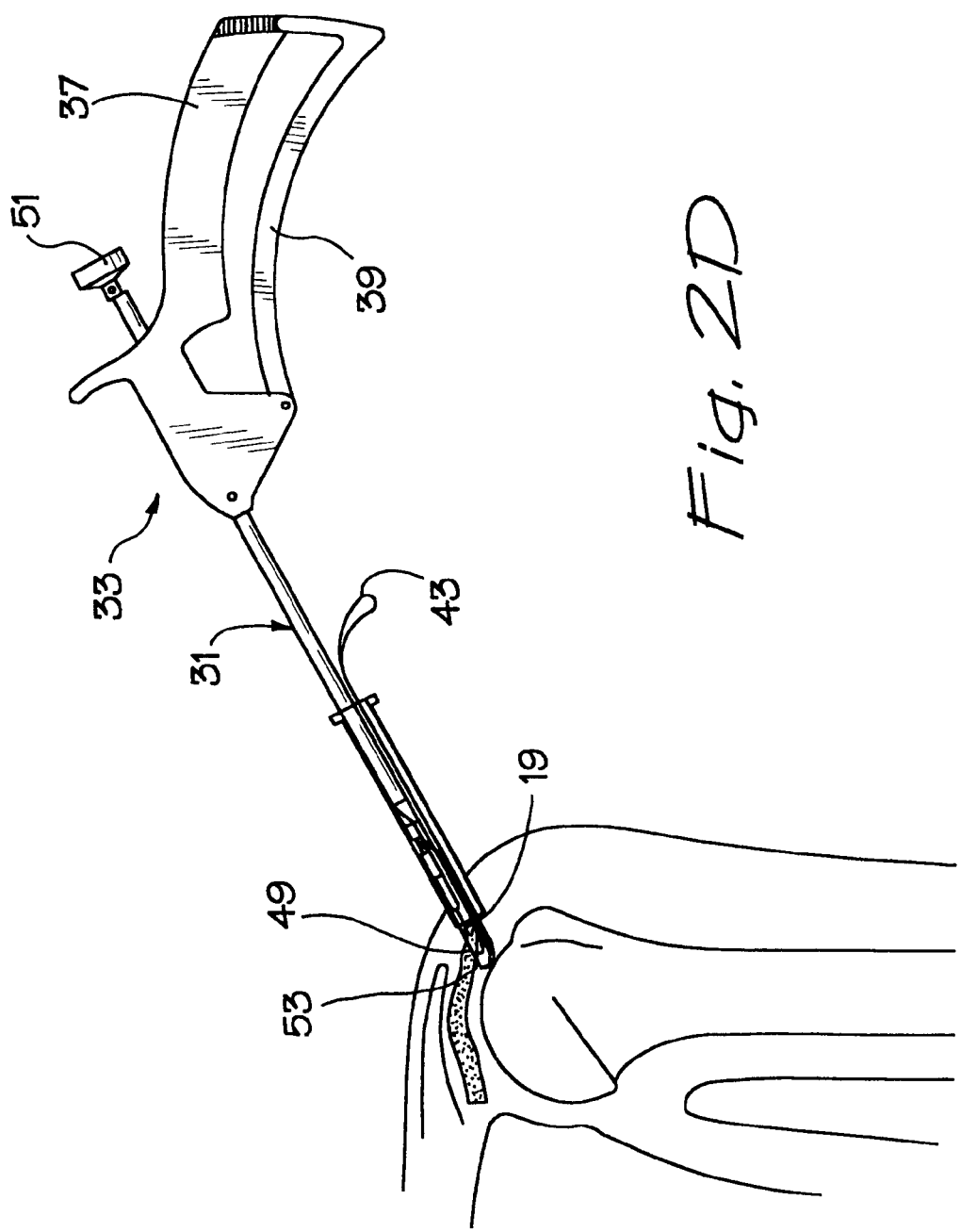
Figure 2E:
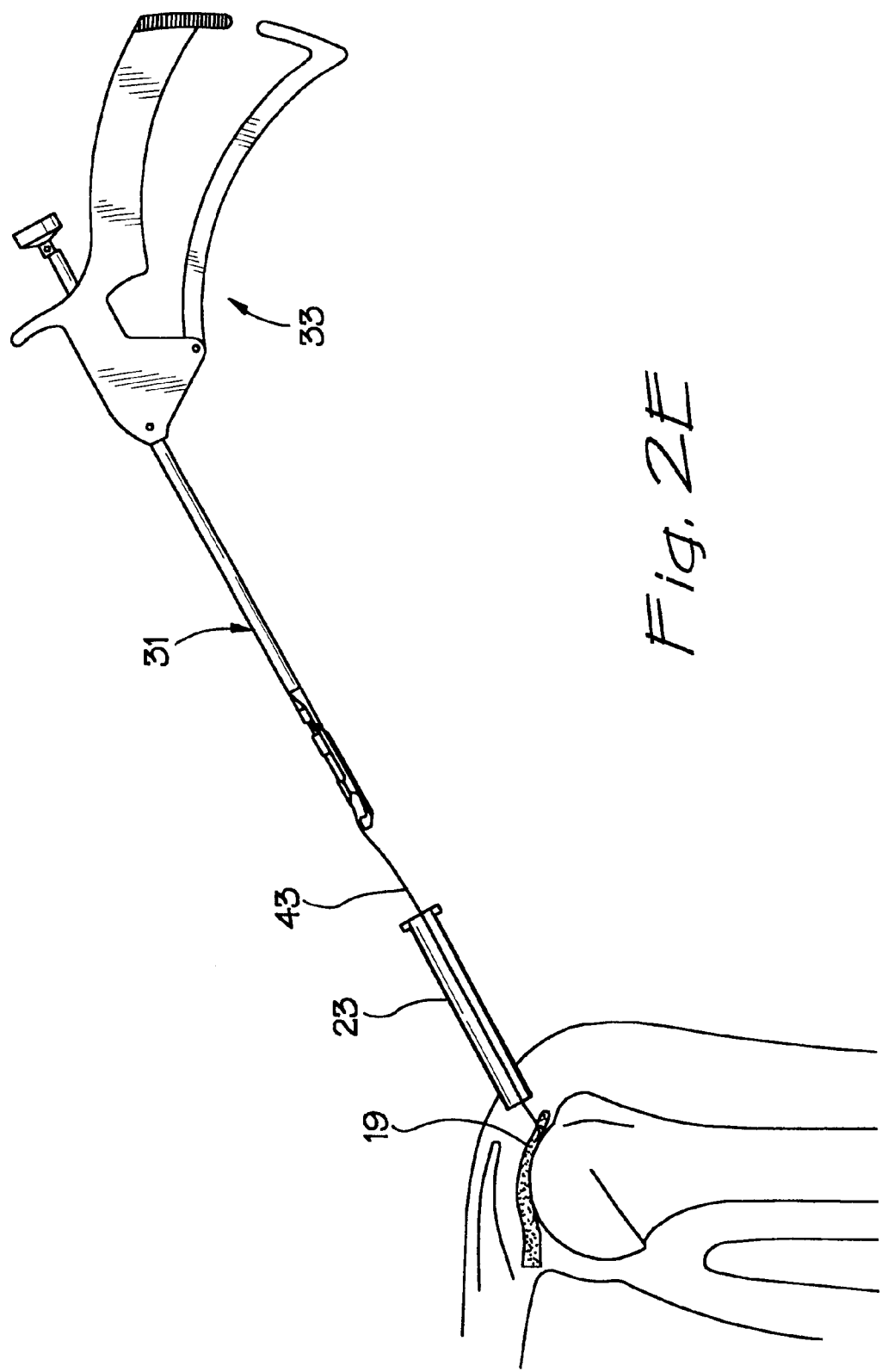

Referring now to FIG. 2D, it is seen that a pair of needles 49 which were stationed within the jaws 27, in a manner to be described more fully hereinbelow, are deployed distally through apertures in the jaws 27 and through the captured portion of the torn rotator cuff 19, once it has been grasped by the jaws 27. In the illustrated embodiment, presently preferred, a knob actuator 51 disposed on the handpiece 33, is moved distally to deploy the needles 49. Once through the tissue 19, the needles penetrate and capture needle couplers or cans 53 attached to distal ends of the suture 43. Then, after retracting the needles 49 and the jaws 27, as illustrated in FIG. 2E, the device 25 may be withdrawn proximally from the operative site, through the trocar port 23. Because the needles 49 are still attached at their proximal ends to the distal end of the suturing device 25, this causes the suture 43 to be drawn proximally together with the suturing device 25. The suture 43 is drawn through the tissues 19 of the torn rotator cuff, thus forming a "mattress stitch" in the torn tendon 19.

Figure 3A:
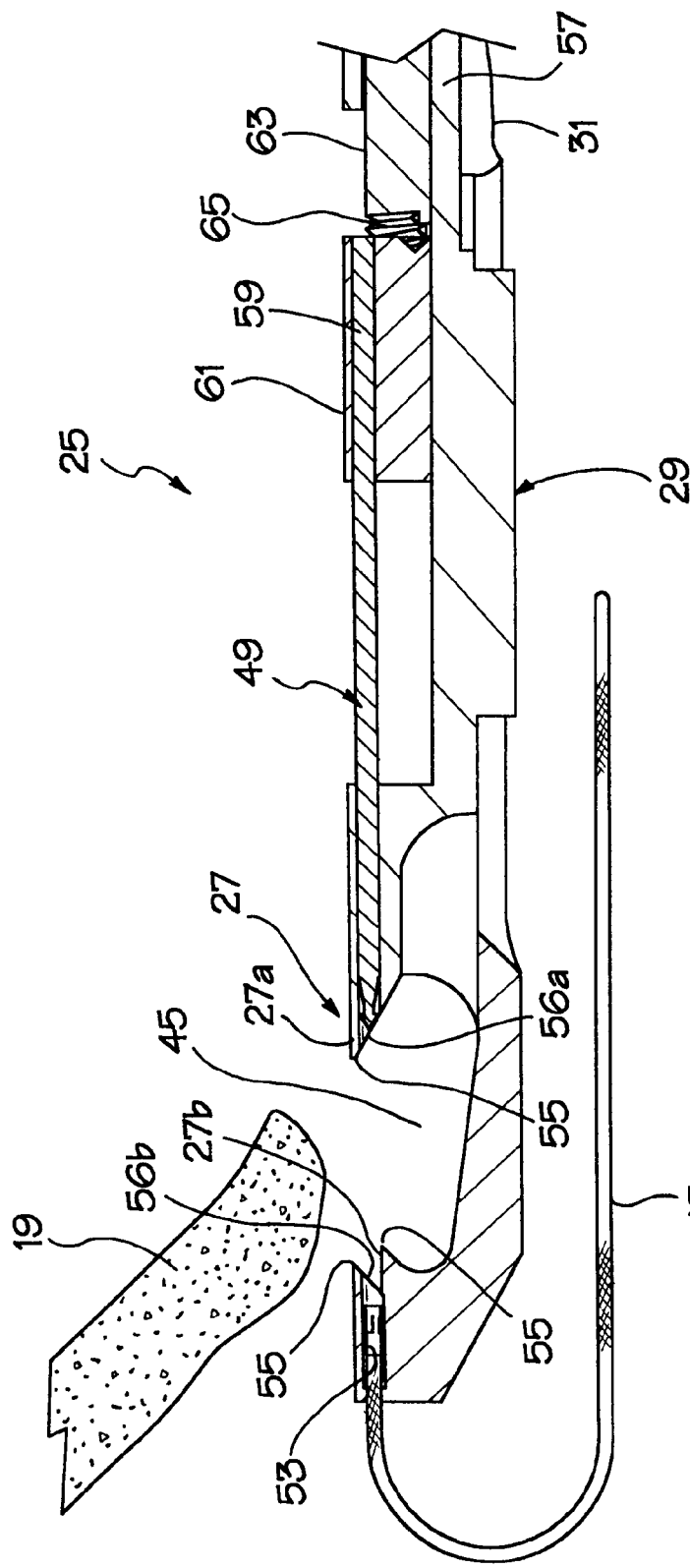
Figure 8C:
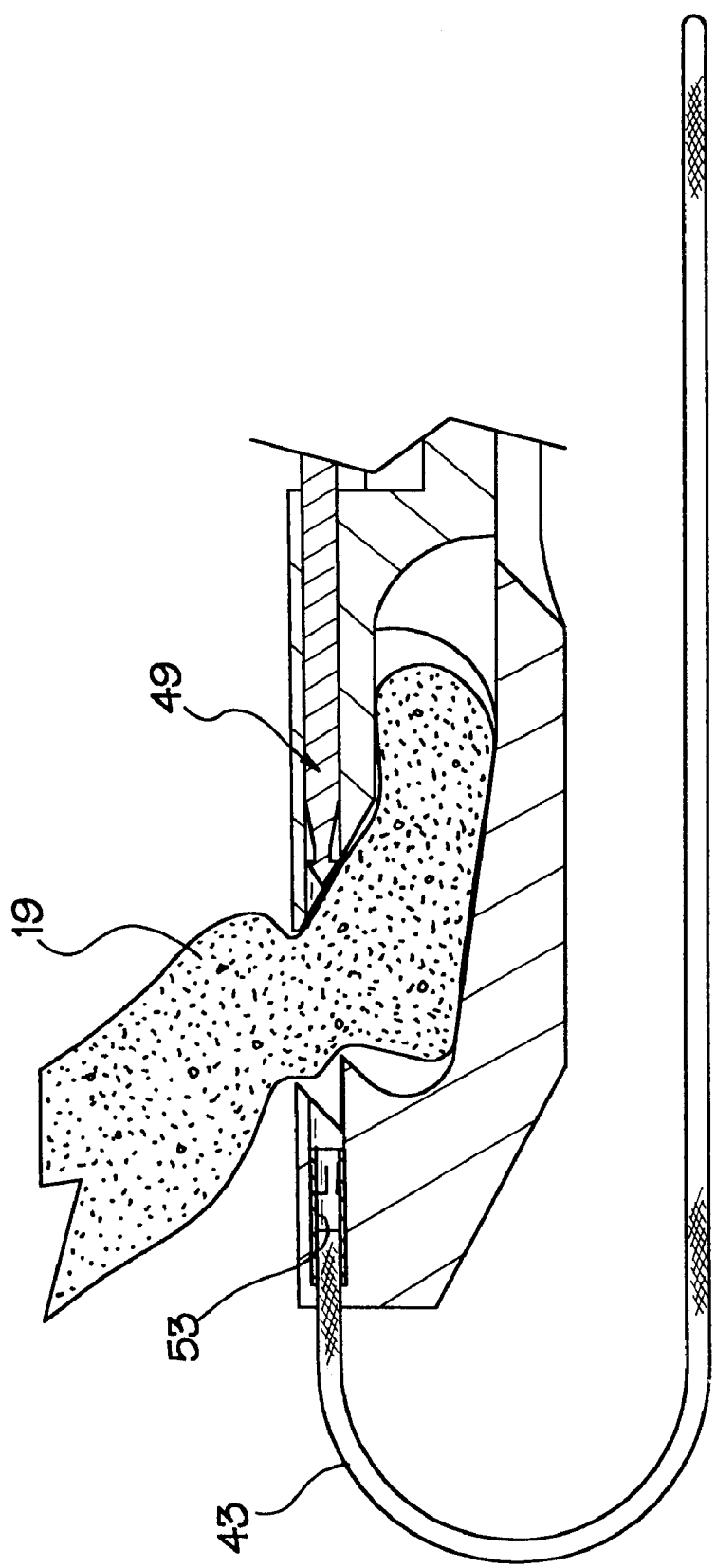
Figure 16:
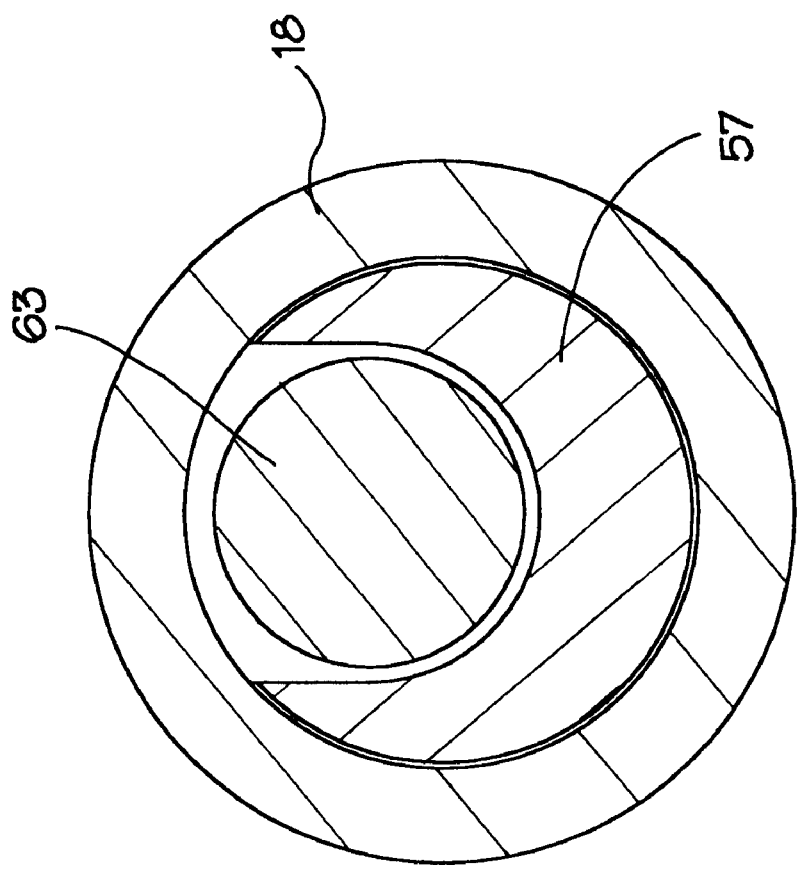
FIG. 16 is cross-sectional view taken along lines 16—16 of FIG. 15.

Referring now largely to FIGS. 3A through 3G, as well as FIGS. 8A through 8G, which are similar to FIGS. 3A through 3G except that only the distal-most portion of the instrument 25 is illustrated in FIGS. 8A through 8G, in an enlarged fashion, the construction and operation of the suturing device 25 will be more particularly discussed, as the sequence of steps illustrated in FIGS. 2A through 2E are described again in additional detail. As shown in FIGS. 3A and 8A, the jaws 27, disposed at the distal end 29 of the hollow barrel 31, comprise an axially movable proximal jaw 27a and a stationary distal jaw 27b. In their opened state, the proximal jaw 27a is retracted proximally relative to the distal jaw 27b, whereas in their closed state, the proximal jaw 27a is extended distally toward the distal jaw 27b. Both jaws preferably include sharp edges or teeth 55 which are configured to atraumatically grip tissue such as the torn rotator cuff tendon 19. Each jaw 27a, 27b also includes apertures 56a and 56b, respectively, which permit passage of the needles 49 therethrough, when the needles are extended through the tissue 19 and into the needle cans 53. Preferably, jaw 27a includes a pair of apertures 56a and jaw 27b includes a pair of apertures 56b, one for each needle 49, though, of course, a single large aperture could be disposed in each jaw as well. The jaws 27 are actuated between their open and closed positions by means of a jaws push rod 57 (FIGS. 3A, 6, and 16, for example), which moves axially in a distal direction, to move the jaw 27a distally to the closed position, when the handle lever 39 is squeezed, and in a proximal direction, to move the jaw 27a to the opened position, when the handle lever 39 is released.

Figure 6:
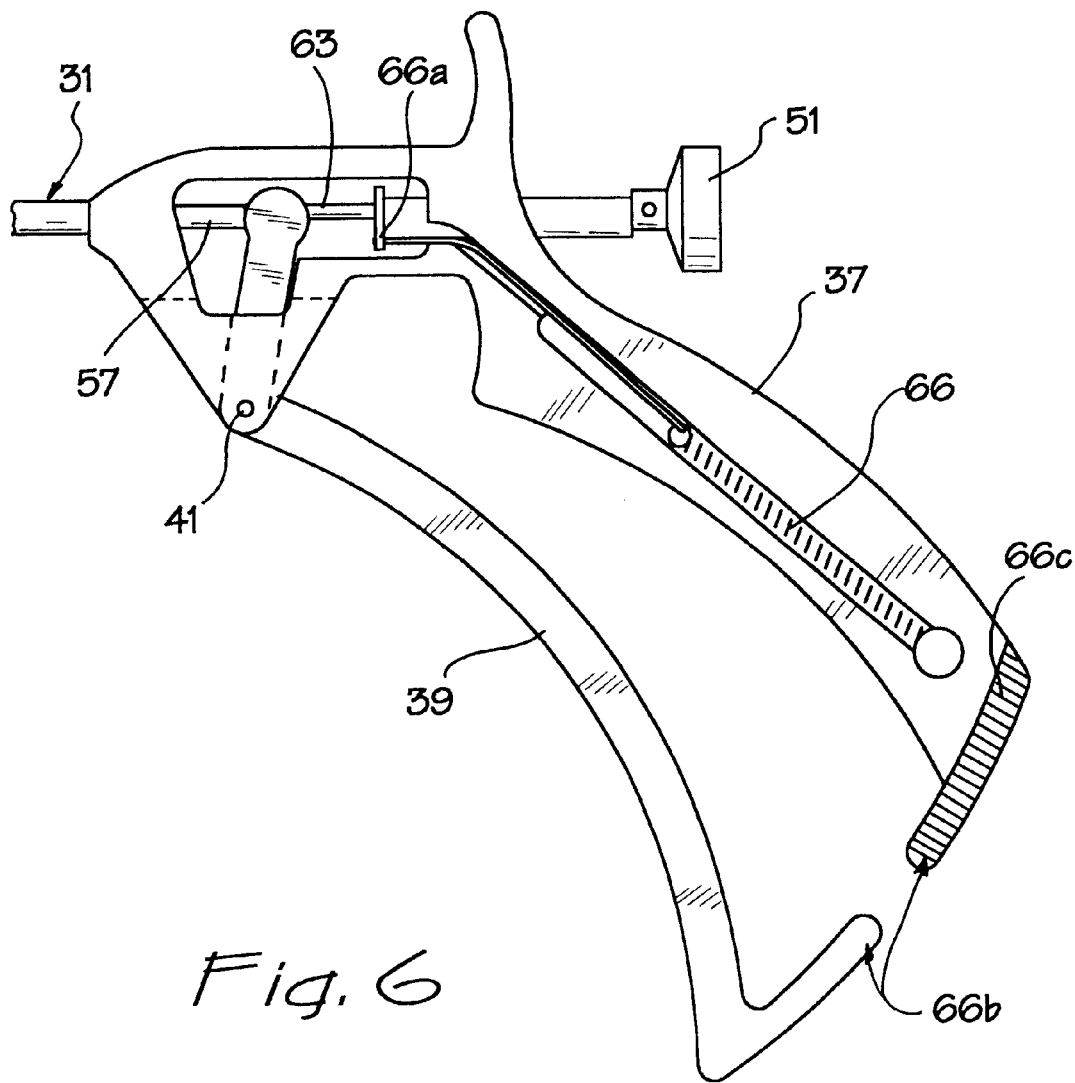
FIG. 6 is a plan diagrammatic view of a proximal actuator end of the inventive suturing instrument.
Figure 7:
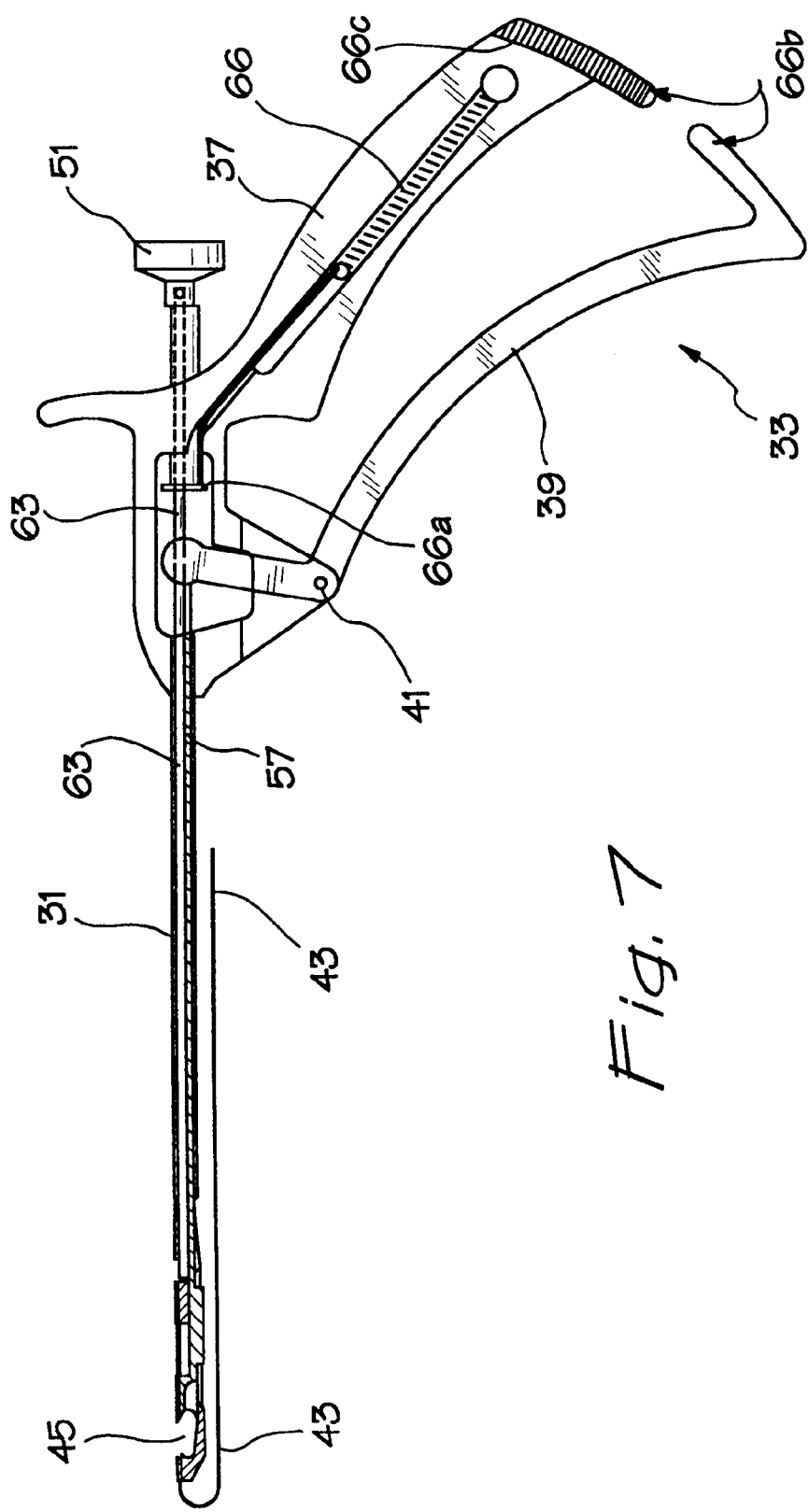
FIG. 7 is a plan diagrammatic view of the entire inventive suturing instrument, illustrating some of the internal features of the instrument.
Figure 12:
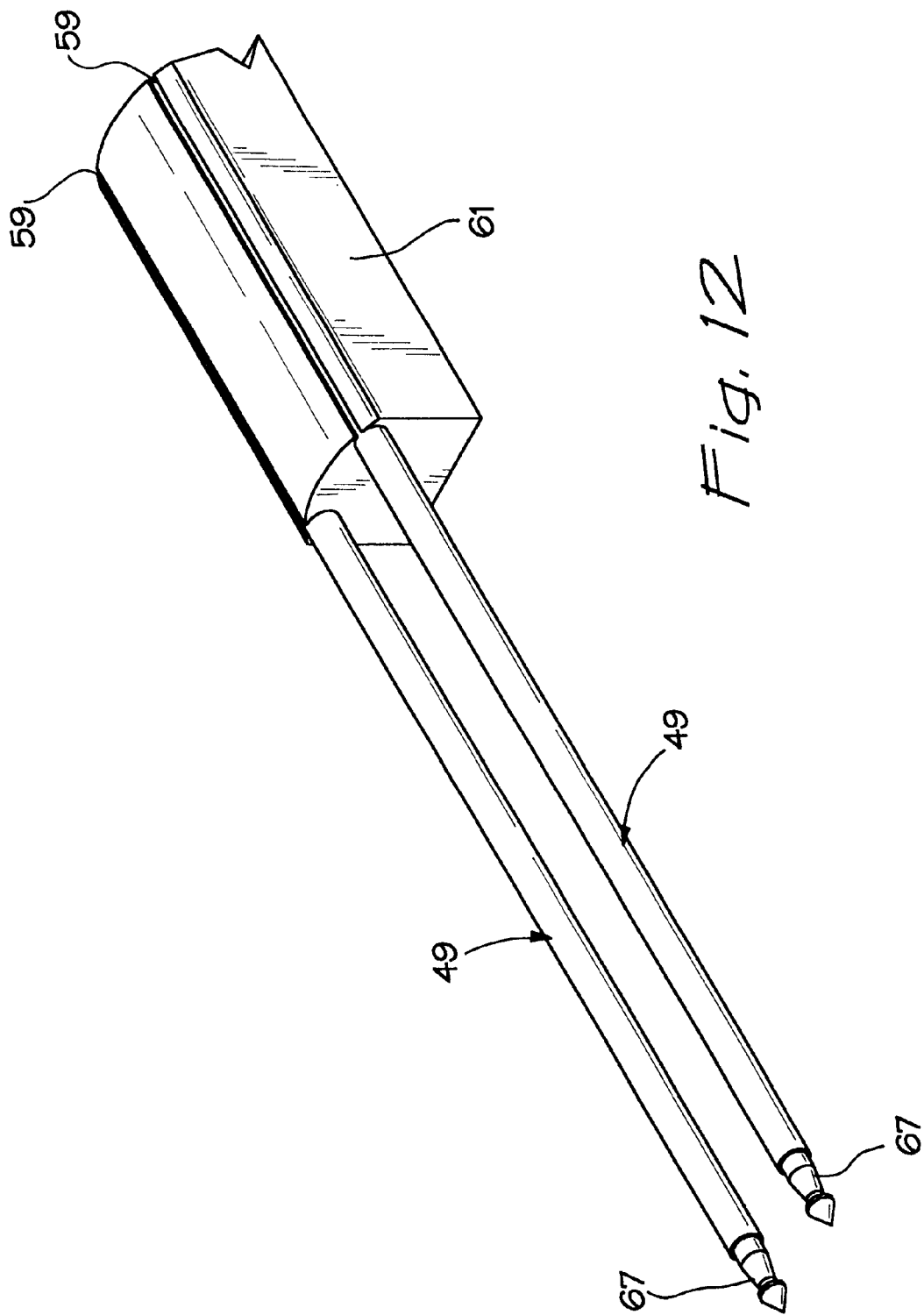
FIG. 12 is a schematic perspective view, in isolation, of the needle magazine of the present invention.

The needles 49 have proximal ends 59 which are disposed within a needle magazine or carriage 61, as shown in FIGS. 3A, 8A, and 12. The magazine is slidable axially respective to the hollow barrel 31 and the jaws push rod 57, so that the needles 49 may be extended and retracted relative to the jaws 27. A needle push rod 63 (FIGS. 3A, 7, and 16, for example) is slidable axially responsive to actuation of the aforementioned knob actuator 51 to push the needle magazine 61 distally. It is secured to the needle magazine 61 as well, via a mechanical attachment 65, so that the knob actuator 51 may be actuated to retract the needle magazine proximally. In fact, referring to FIG. 6, in the presently preferred embodiment, a spring or other suitable biasing means 66 is disposed in the handle grip 37 for biasing the needle push rod 63 in a proximal position, so that the default position of the needles 49 are their retracted position. The spring 66 is attached to the needle push rod 63 at a joint 66a, as shown in FIGS. 6 and 7.

Figure 3B:
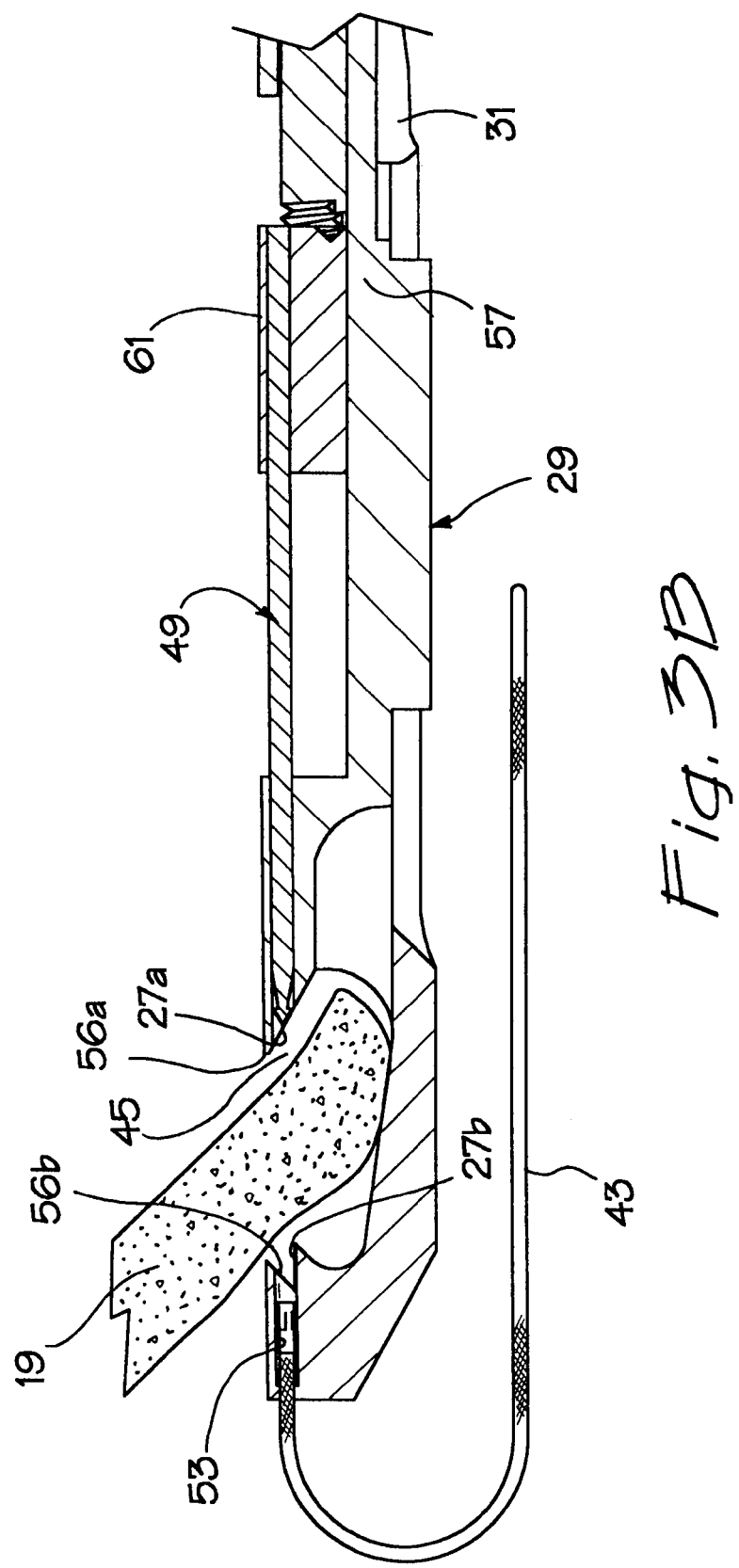

Now, the preferred procedure will be described again in greater detail. In FIGS. 3A and 8A, the distal end 29 of the suturing device 25 is shown with the jaw 27a in its proximally retracted, open position relative to stationary jaw 27b. The device has been inserted through the trocar port 23 into the shoulder joint, as illustrated previously in FIG. 2B, and the jaws 27 are oriented such that a portion of the torn rotator cuff 19 is adjacent to the recess 45 within the distal end 29 of the instrument 25. In FIGS. 3B and 8B, the distal end 29 of the instrument 25 has been manipulated so that a portion of the torn rotator cuff 19 is disposed within the recess 45, as shown previously in FIG. 2B. At this juncture, the jaw 27a remains in its proximally retracted, open position.

Figure 3C:
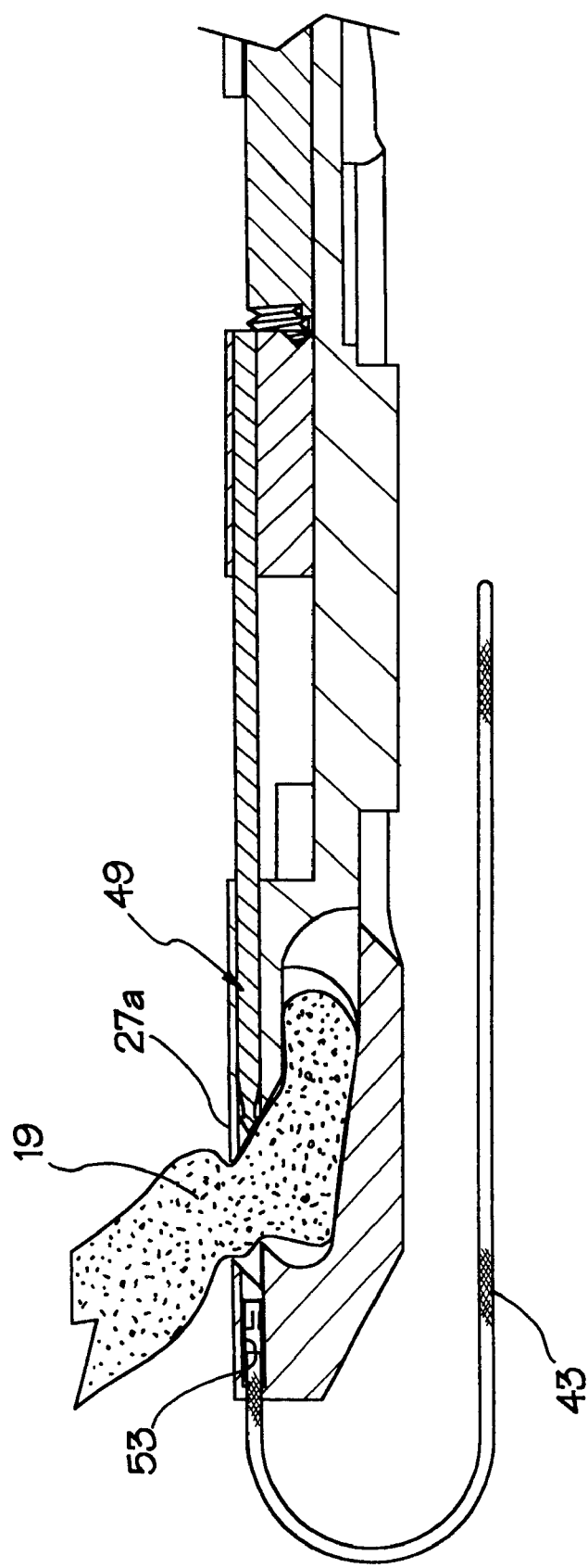

As shown in FIGS. 3C and 8C, the jaw 27a is then actuated to move to its distally extended, closed position relative to jaw 27b. This is accomplished in the presently preferred embodiment, as discussed supra, by actuating handle lever 39 (FIG. 2C), which, in turn, moves the jaws push rod 57 in a distal direction, thereby moving the jaw 27a distally. The result is that the tissue 19 which is disposed in the recess 45 is firmly grasped between the jaws 27a and 27b. There is an ability to vary the degree to which the jaws 27 close by varying the travel through which the handle lever 39 is displaced. This is an advantageous feature to adjust for different thicknesses of tissue to be clamped. Additionally, a latching mechanism 66b, preferably in the form of a ratcheting device having engaging teeth 66c is provided, as shown in FIGS. 6 and 7, for example, which permit the jaws to be locked into a desired clamping position, by locking the position of the handle lever 39 relative to the handle grip 37, once an appropriate section of tissue has been isolated and grasped by the jaws.

Figure 3D:
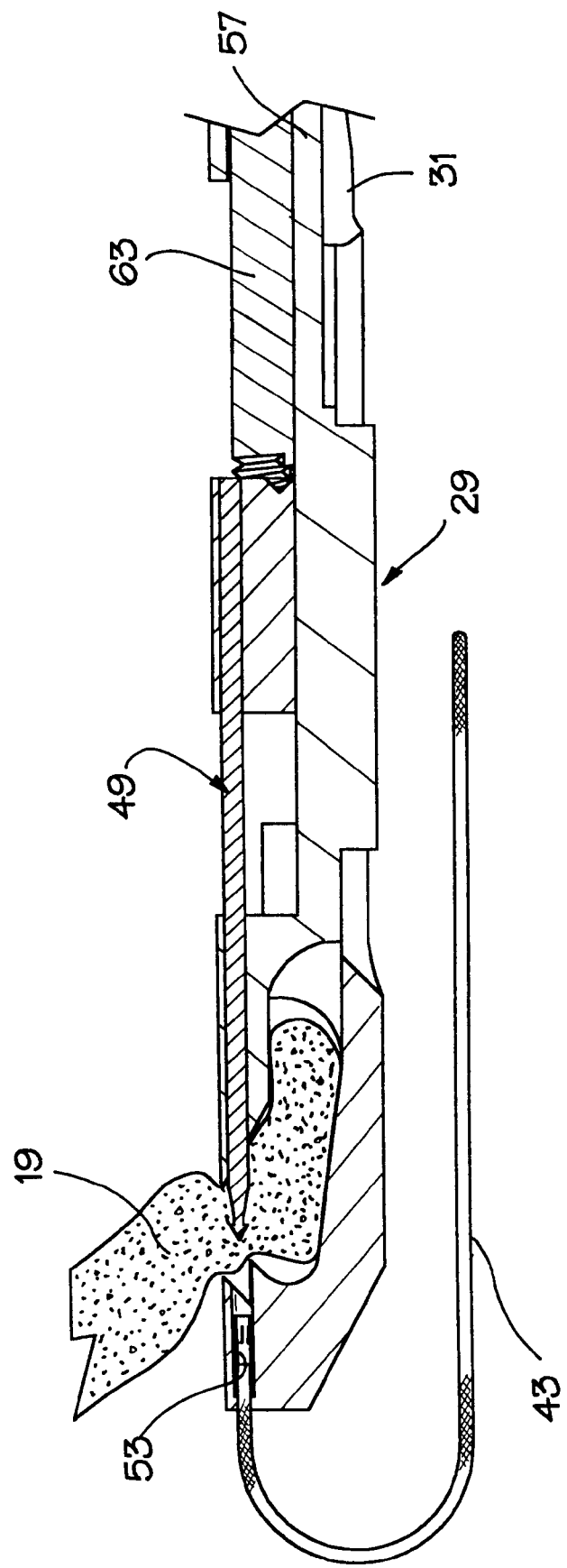
Figure 8D:
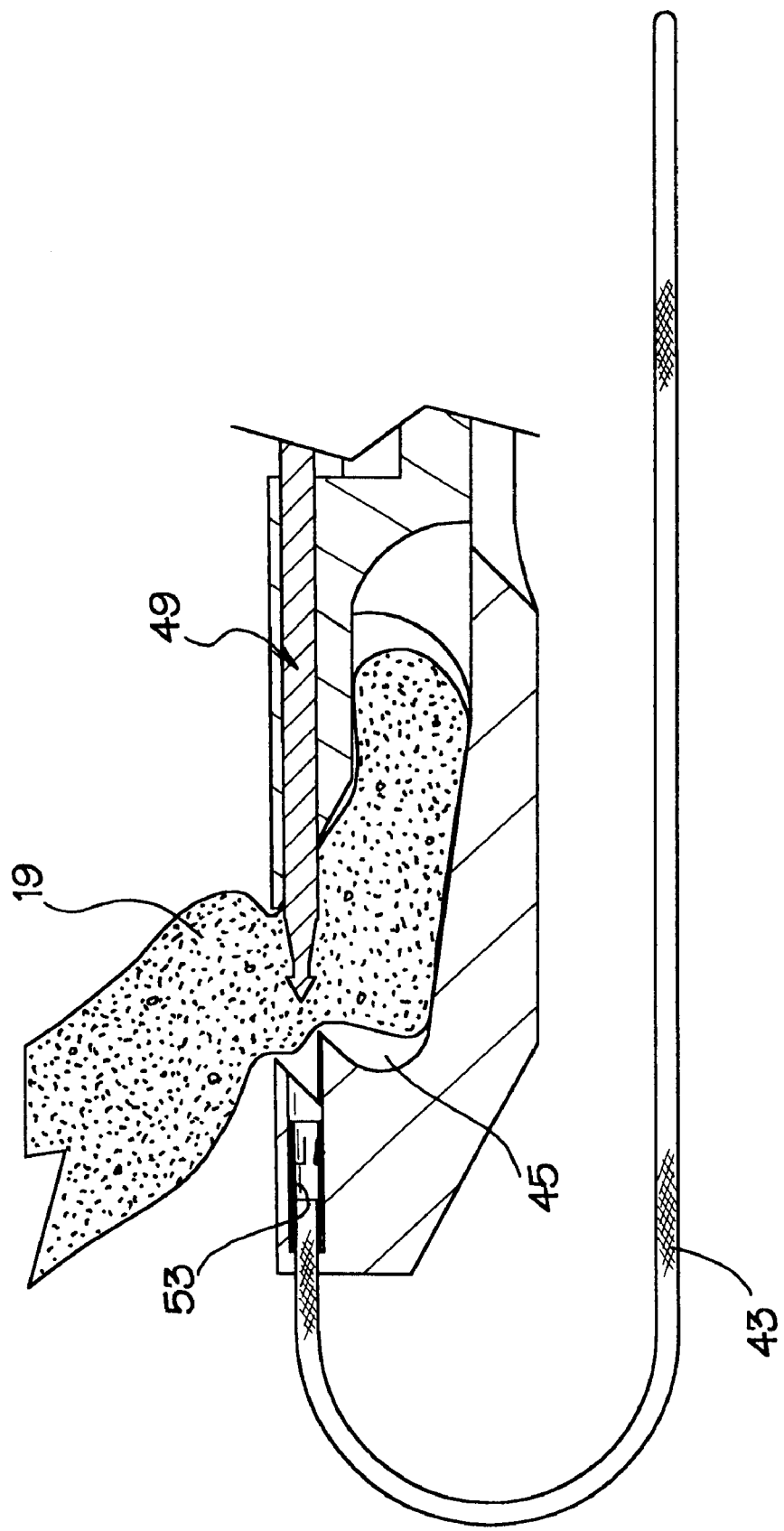
Figure 9:
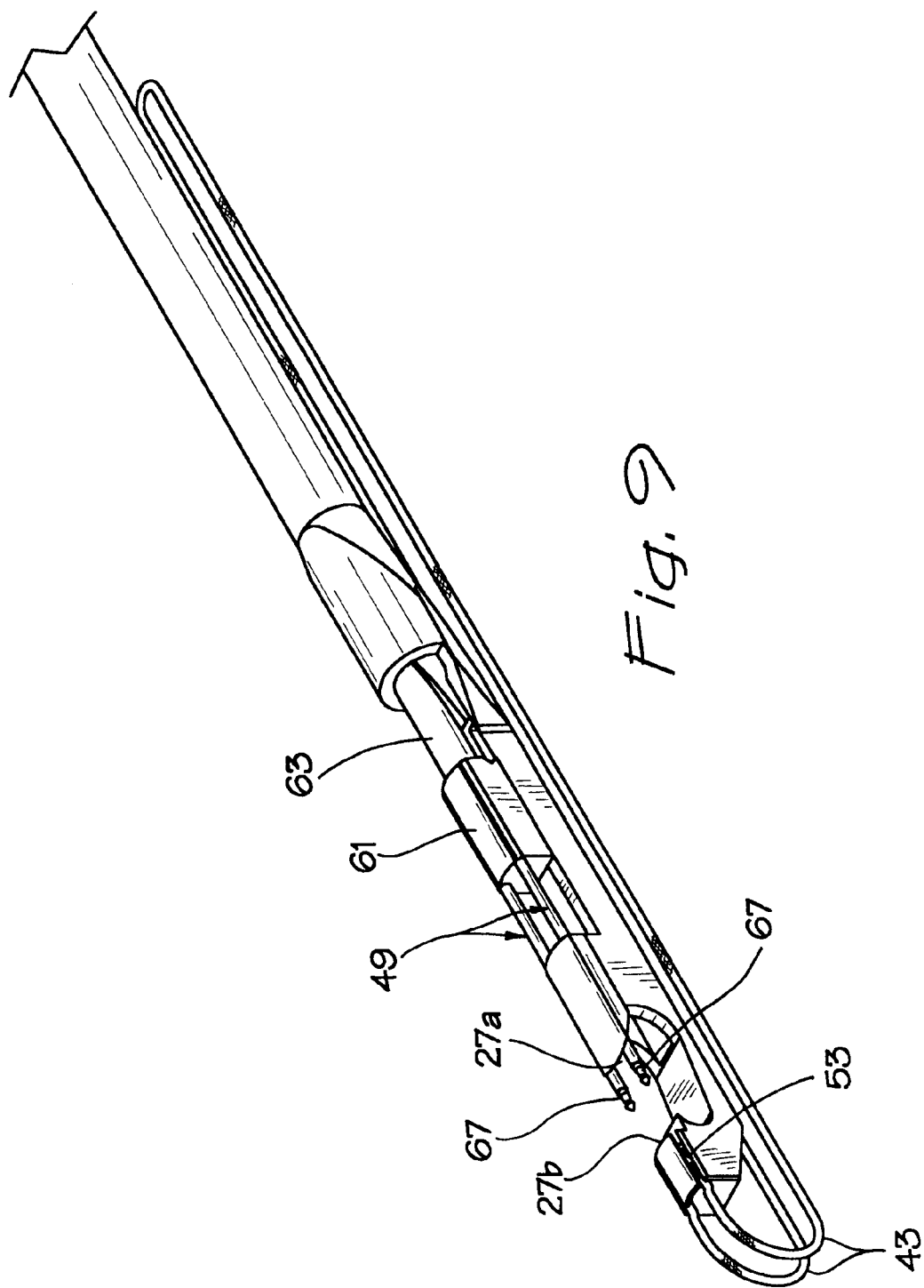
FIG. 9 is a perspective view of the distal end of the inventive suturing instrument.
Figure 10:
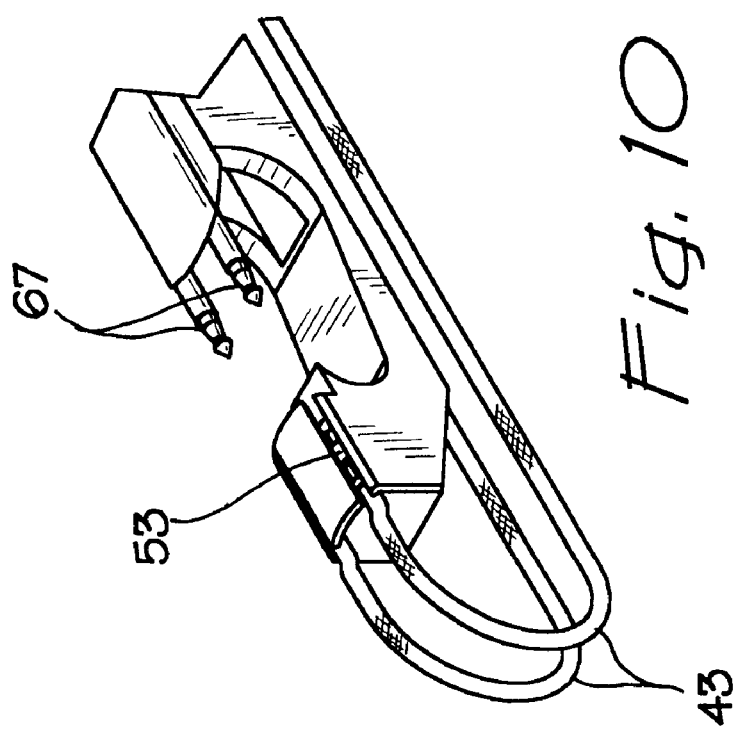
FIG. 10 is an enlarged perspective view of the distal-most portion of the distal end of the inventive suturing instrument.
Figure 15:
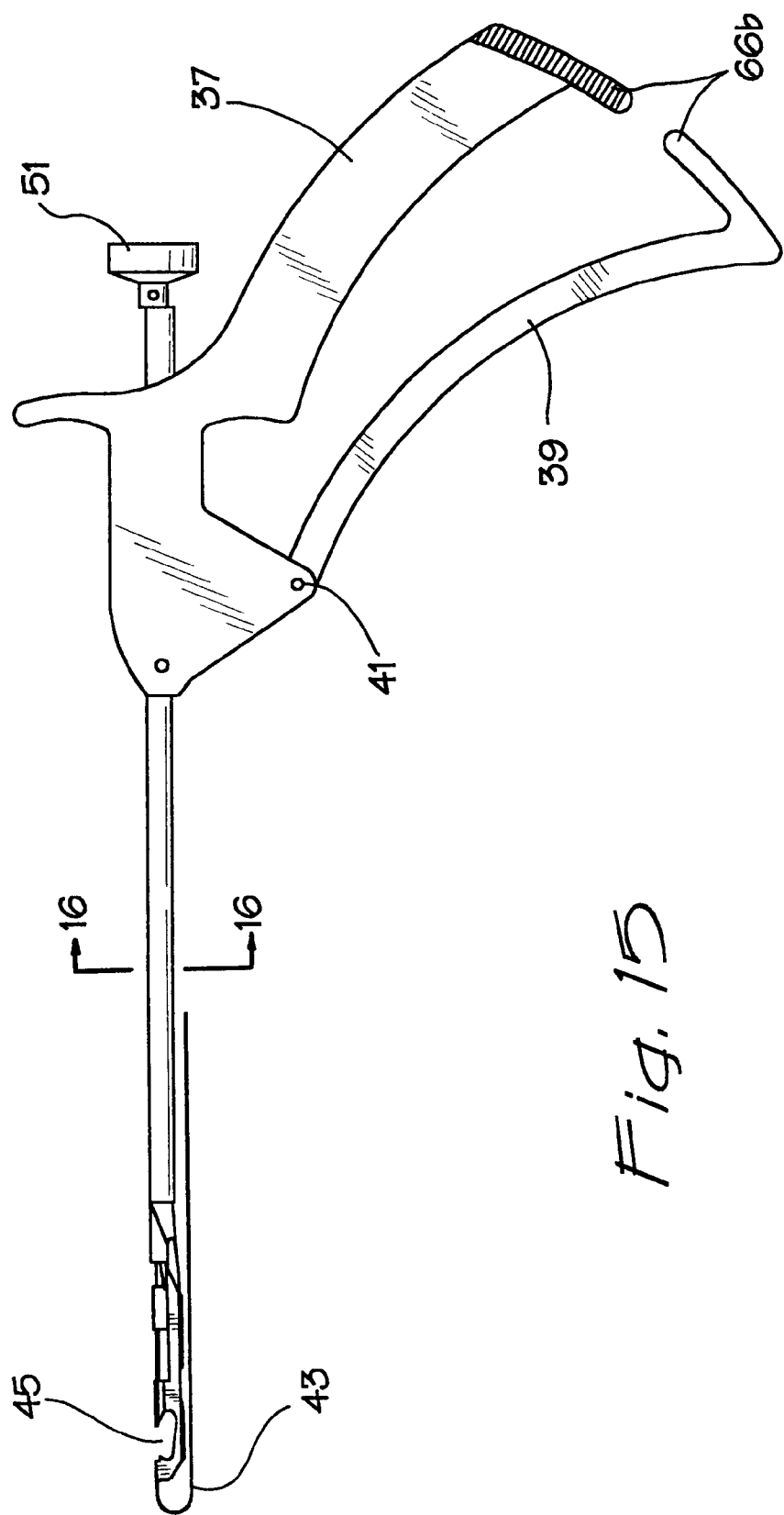
FIG. 15 is plan view of the suturing instrument shown in FIG. 14.

Referring now to FIGS. 3D and 8D, once the tissue 19 has been grasped in a satisfactory manner by the jaws 27, the pair of needles 49 which were stationed within the jaws 27 are deployed distally through the captured portion of the torn rotator cuff 19. As discussed supra, the knob actuator 51 (FIG. 2D) is actuated distally to move the needles 49 distally. Distal actuation of the knob actuator 51 moves the needle push rod 63 distally, which, in turn, pushes the needle magazine 61 distally (see also FIGS. 9, 15, and 16).

Figure 3E:
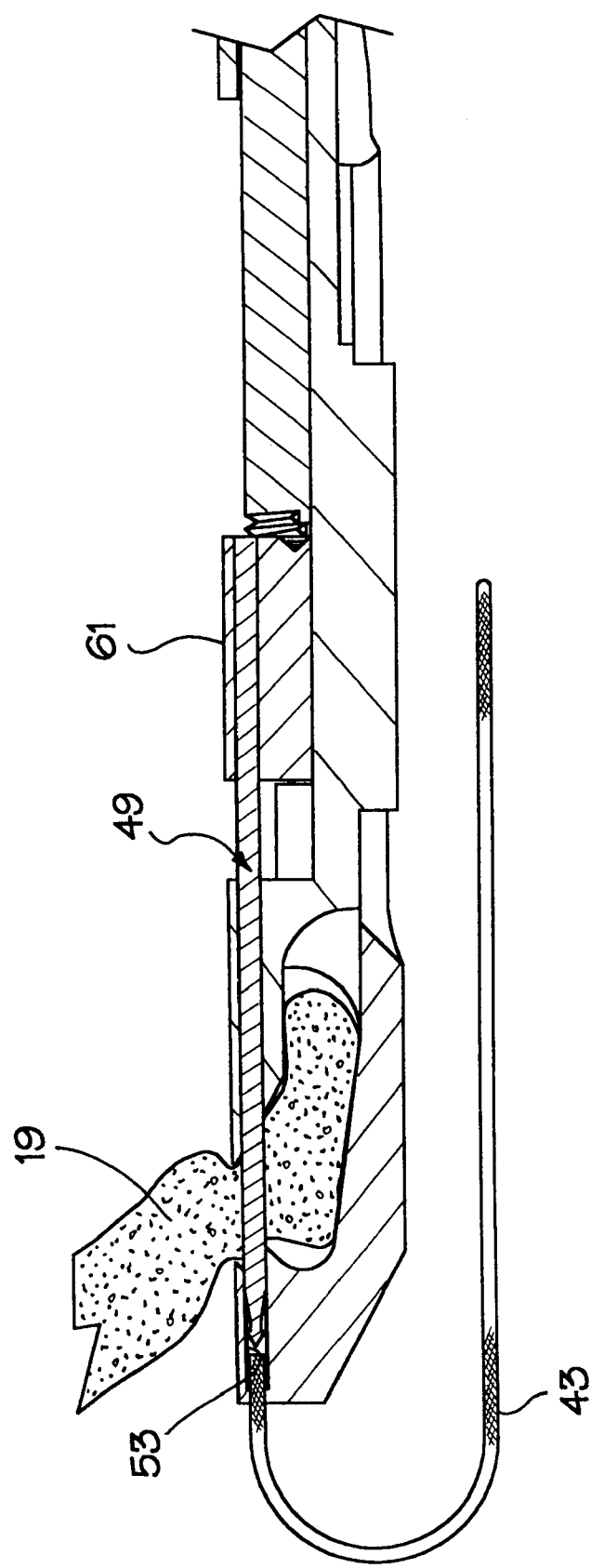
Figure 13:
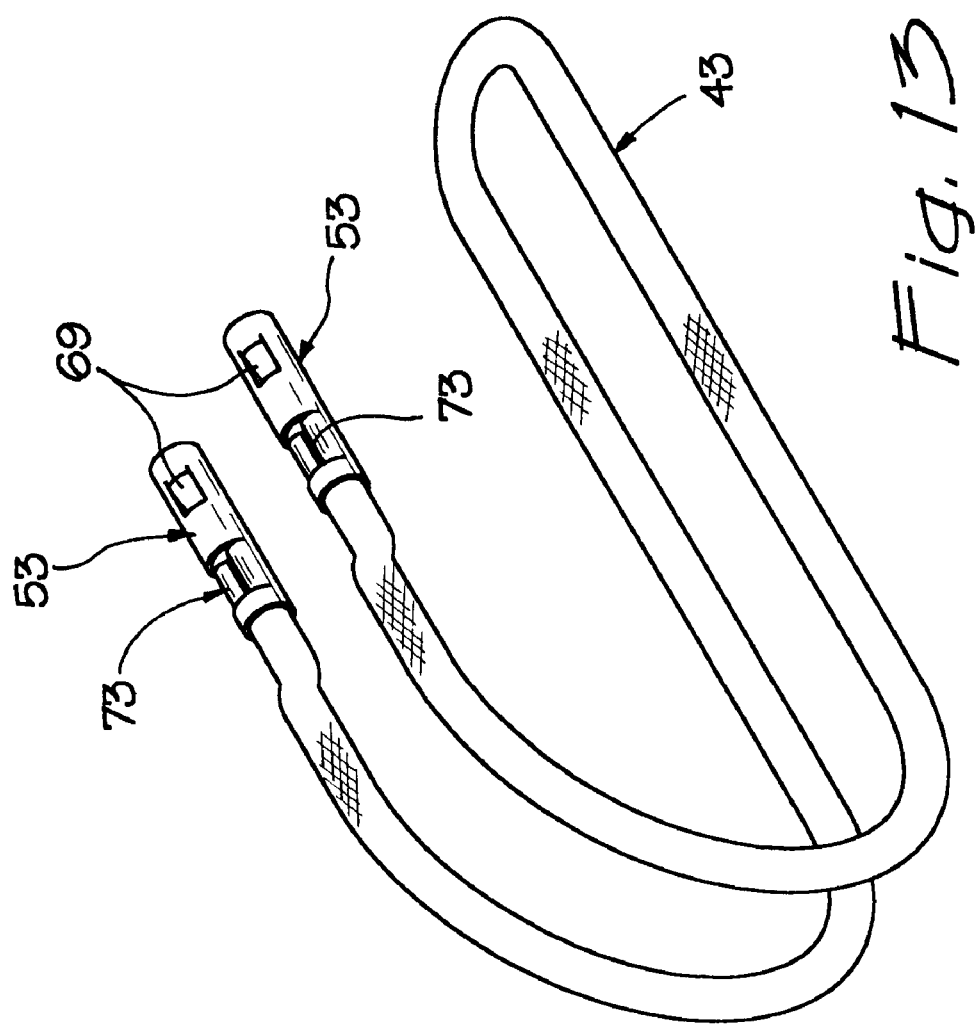
FIG. 13 is a schematic perspective view, in isolation, of a length of suturing material having needle capture cans attached to both free ends thereof, for use with the suturing instrument of the present invention.
Figure 14:
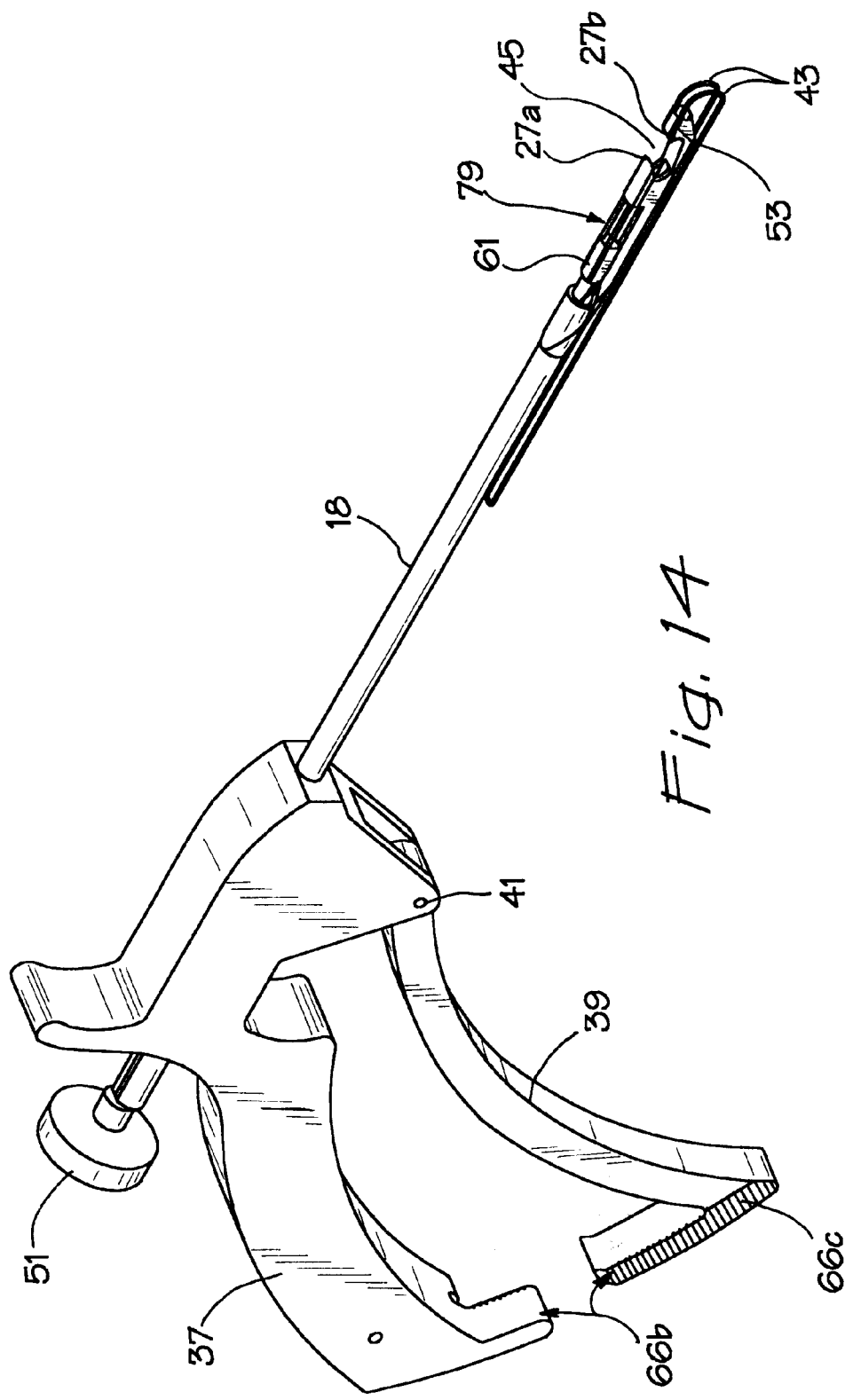
FIG. 14 is a perspective view of the inventive suturing instrument shown in FIG. 7.

Once through the tissue 19, as illustrated in FIGS. 3E and 8E, the needle couplers or cans 53 are captured by the needles 49 in their fully distally extended state. The cans 53 are attached to distal ends of the suture lengths 43. This capture process is best shown in FIGS. 4A through 5B. As shown therein, a distal end 67 of the needle 49 is preferably configured to include a relatively broad head with a slender neck disposed immediately proximally thereof. Thus, as the distal end 67 of the needle is inserted into the needle couplers/cans 53, capture tabs 69 on the sidewalls of the cans 53 are pushed outwardly by the distally moving head portion of the needle distal end 67. Then, once the head portion has moved distally past the capture tabs 69, the tabs 69 return to their inward position, as shown in FIG. 5B, so that the distal ends of the capture tabs 69 are disposed against a proximal face 71 of the head of the needle. This action creates a permanent attachment of the needle 49 to the can 53, so that the suture 43 is irreversibly joined to the needle 49. It is noted that the cans 53 are preferably attached to the distal ends of the suture length 43 via crimped regions 73, which are typically created using a swaging process, as shown in FIGS. 4A, 4B, and particularly in FIG. 13. In presently preferred embodiments, the cans 53 are each fabricated of a small piece of hypodermic tubing that has been configured to have a set of the aforementioned tabs 69, preferably three or four per suture, fabricated into the periphery of the tube, and which are bent inwardly as above described, toward the central axis of the tube at an acute angle.

Figure 3F:
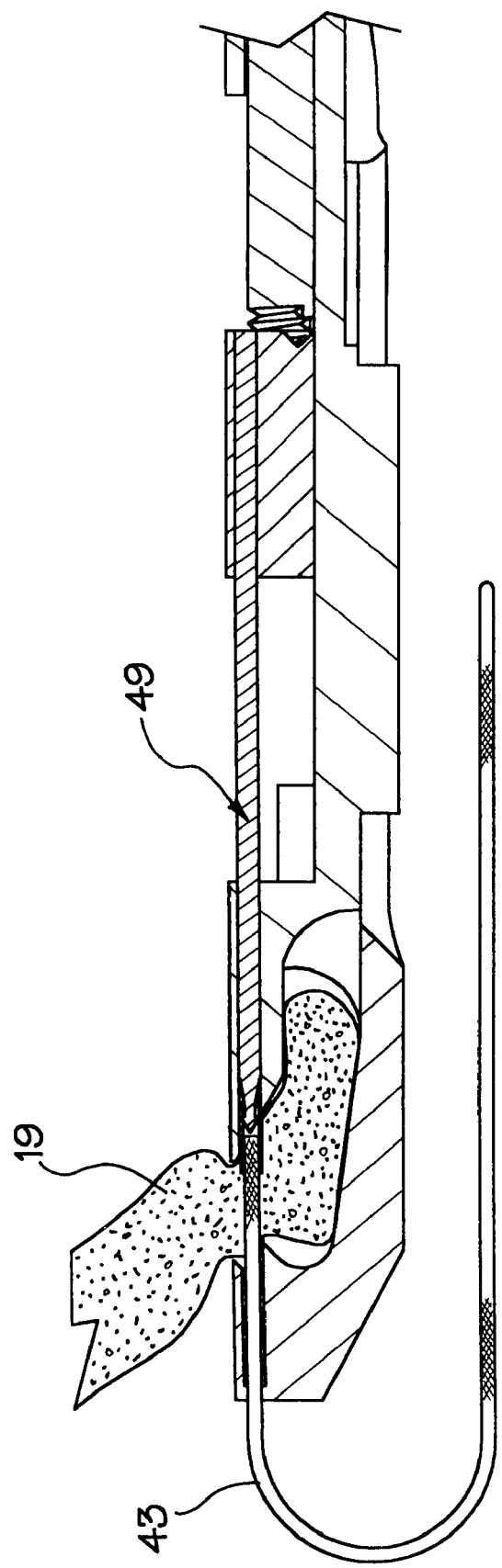
Figure 36:
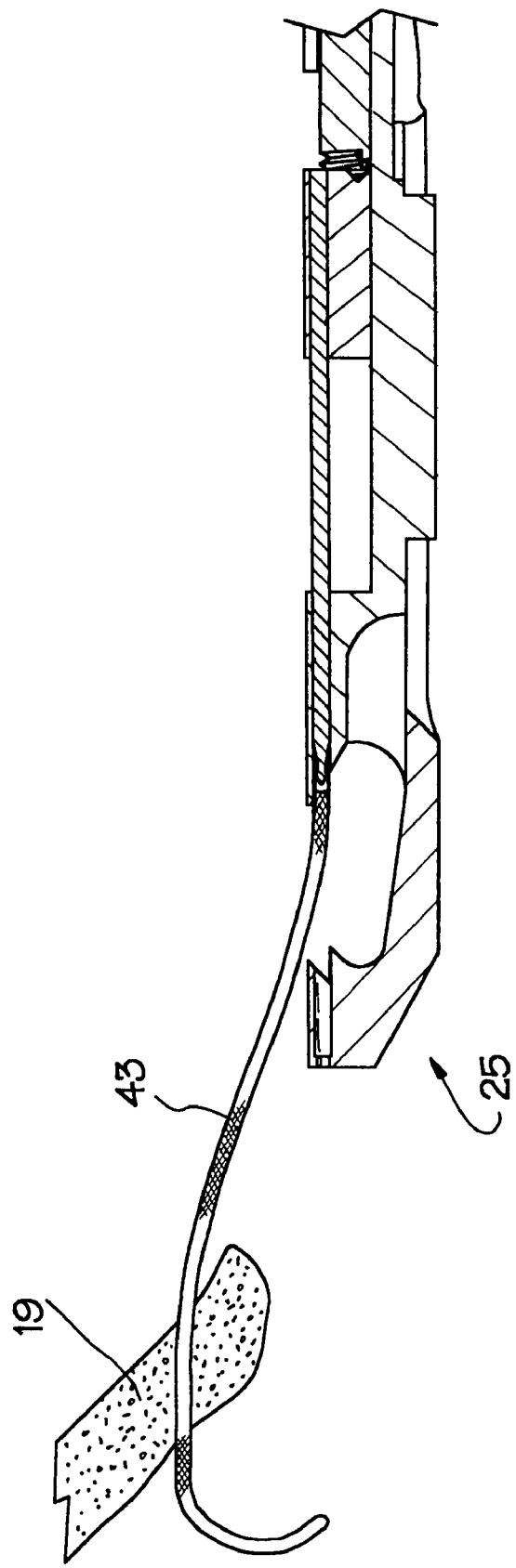
Figure 8F:
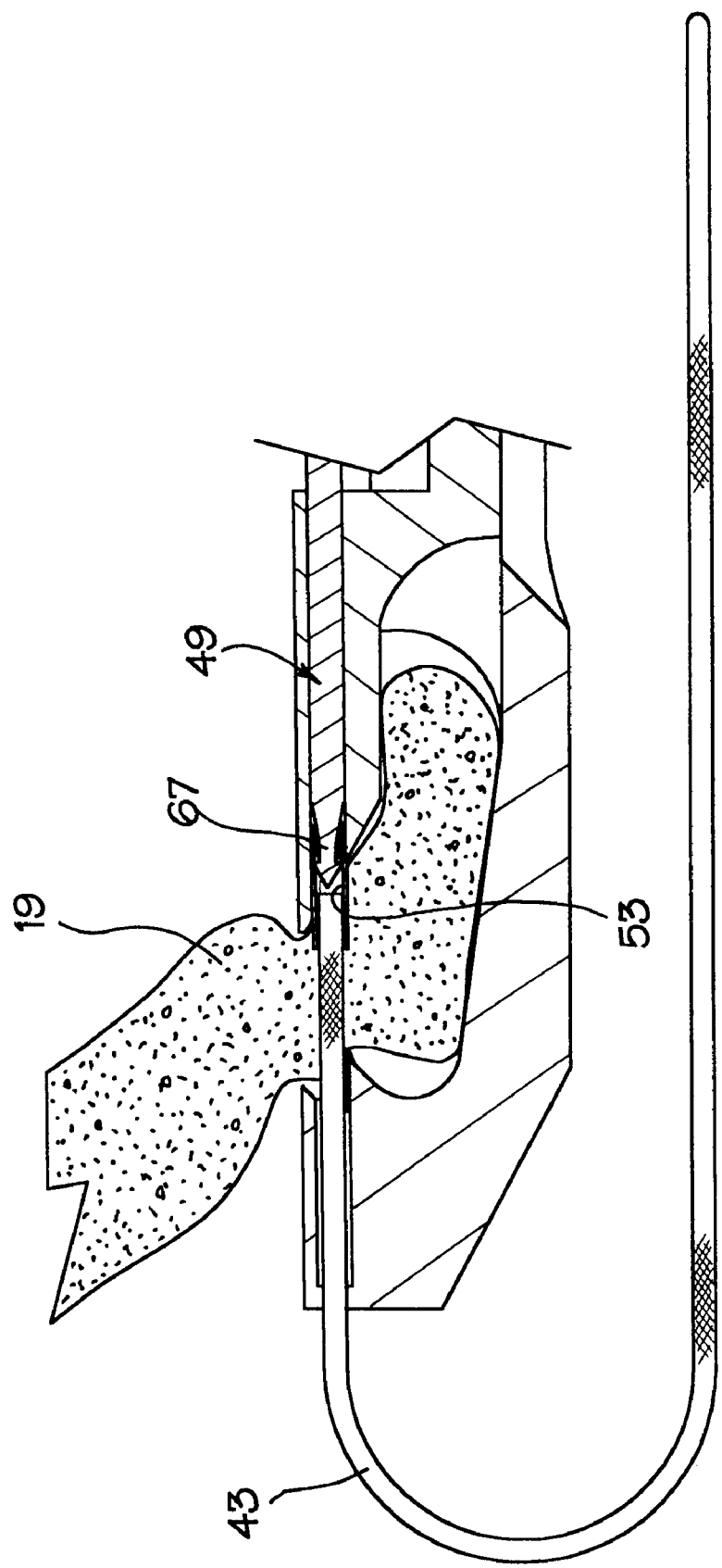
Figure 86:
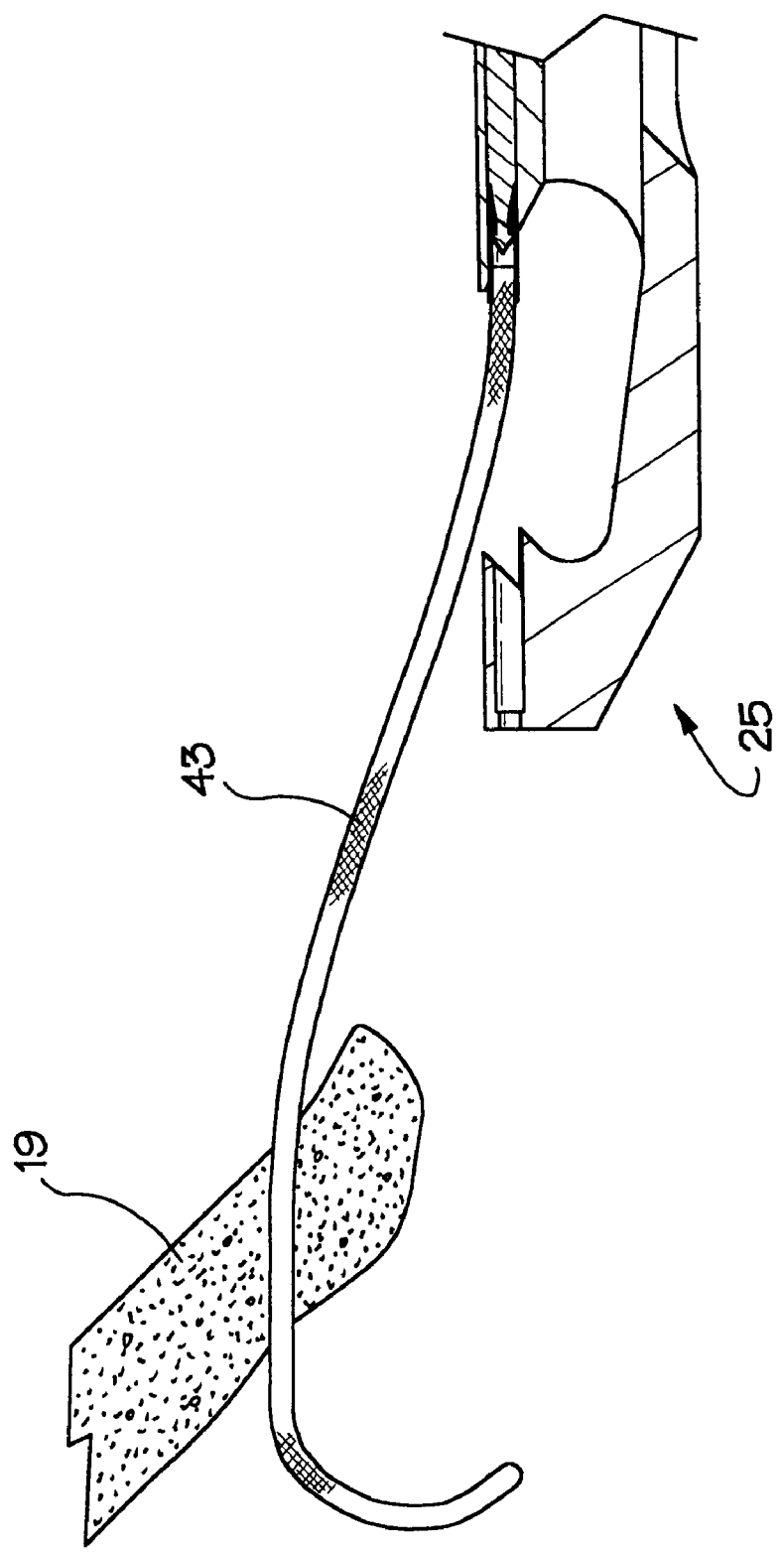
Figure 11:
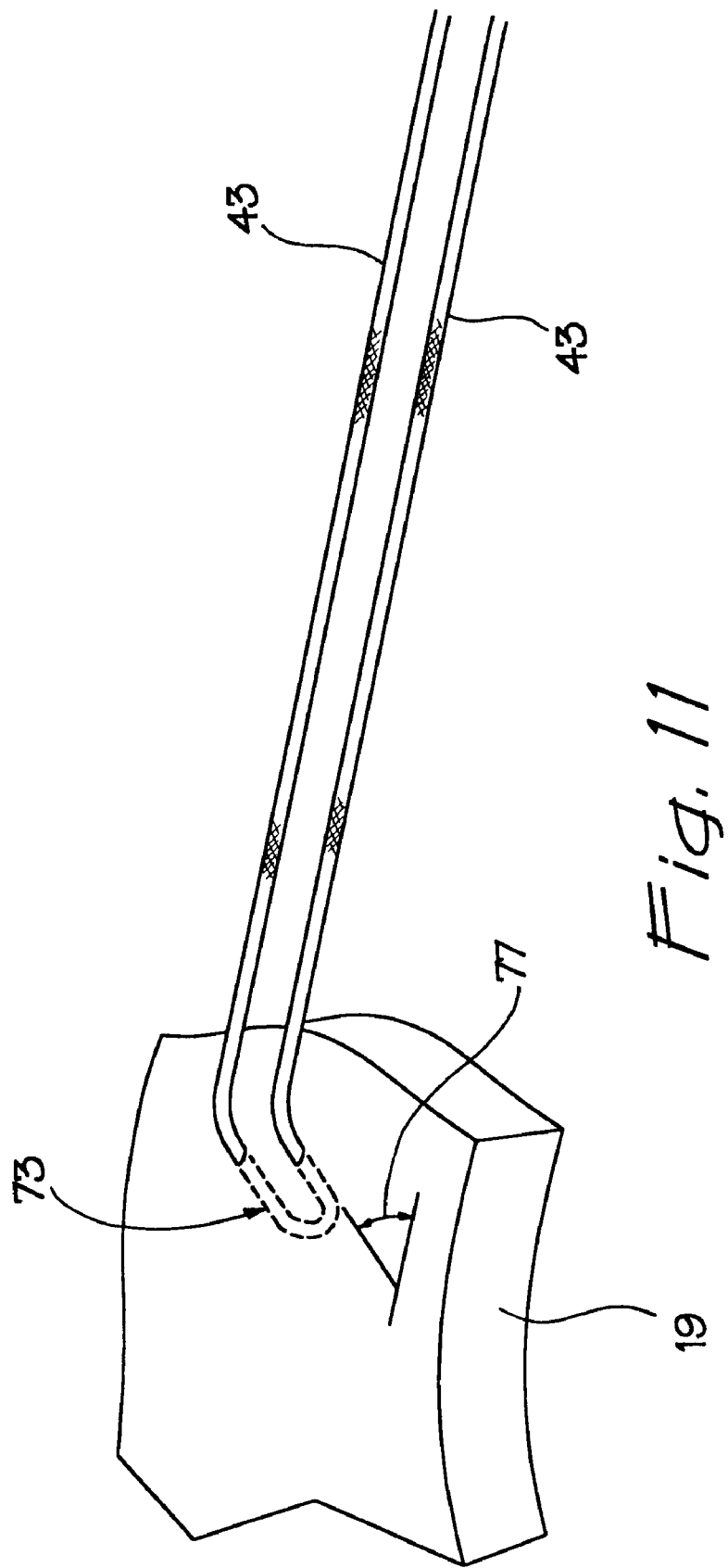
FIG. 11 is a schematic perspective view showing a mattress stitch which is created in a portion of soft tissue using the inventive suturing instrument in accordance with the inventive methods taught herein.

Then, as illustrated in FIGS. 3F and 8F, the needles 49 are withdrawn proximally back through the tissue 19 by actuating the knob actuator 51 proximally. Since the needles 49 are joined with the end of the suture 43 via the cans 53, the end of the suture is also withdrawn proximally through the tissue 19. As shown in FIGS. 3G and 8G, the entire device 25 is then withdrawn proximally from the operative site, through the trocar port 23. Because there are two needles 49 in the preferred embodiment, and thus two suture ends 43, this action creates a mattress stitch 73 through the torn tendon 19, as illustrated best in FIG. 11.

An important feature of the invention is that the face 75 of the jaw 27a is oriented at an acute angle 77 relative to a longitudinal axis 79 of the instrument 25, as is shown in FIG. 8A, for example. This acute angle, in preferred embodiments, is approximately 30–45 degrees, with 45 degrees being presently preferred, although the important feature is that the acute angle be substantially more than 0 degrees and substantially less than 90 degrees. The reason for this is that it results in a suture angle through the tissue 19 which is approximately the same as the angle 77 (see FIG. 11). By orienting the stitch 73 at such an angle 77 through the tissue 19, a great deal of stress on the suturing material 43 is alleviated, thereby improving substantially the durability of the stitch and, thus, the chance for a successful outcome.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device for use endoscopically, comprising:
    a first jaw member;
    a second jaw member, said first and second jaw members being disposed at a distal end of said suturing device;
    an actuator disposed at a proximal end of the suturing device, for actuating the first and second jaw members between a closed orientation, wherein the first and second jaw members are disposed in close proximity to one another, and an open orientation, wherein said first and second jaw members are substantially spaced from one another;
    a hollow barrel disposed between said actuator and said first and second jaw members;
    a linking member disposed within said hollow barrel, connecting said actuator with said first jaw member;
    at least one needle disposed at the distal end of said suturing device, said at least one needle being movable between a retracted position and an extended position for passage through tissue grasped between said first and second jaw members; and
    a needle carriage on which said at least one needle is disposed, said needle carriage being axially movable between distal and proximal positions at said distal end of said suturing device.

2. The suturing device as recited in claim 1, wherein said first jaw member is axially movable relative to said second jaw member, to thereby move said jaw members between said closed and open orientations.

3. The suturing device as recited in claim 1, wherein said actuator comprises a handpiece.

4. The suturing device as recited in claim 3, wherein said handpiece comprises a handle grip and a handle lever, said handle lever being movable relative to said handle grip.

5. The suturing device as recited in claim 4, wherein said handle lever is pivotally mounted relative to said handle grip, such that it is pivotable between a first position corresponding to said closed orientation of said first and second jaw members and a second position corresponding to said open orientation of said first and second jaw members.

6. The suturing device as recited in claim 5, and further comprising a latching mechanism for securing said handle lever relative to said handle grip, to thereby also secure said first and second jaw members in a desired orientation.

7. The suturing device as recited in claim 1, and further comprising a second actuator disposed at the proximal end of said suturing device, for actuating said needle carriage to move axially between said distal and proximal positions.

8. The suturing device as recited in claim 7, wherein said second actuator comprises a knob actuator.

9. The suturing device as recited in claim 8, and further comprising a spring for biasing said needle carriage in said proximal position.

10. The suturing device as recited in claim 1, wherein said at least one needle comprises two spaced needles.

11. The suturing device as recited in claim 1, and further comprising a recess in said distal end of said suturing device, for receiving portions of said tissue which is to be grasped between said first and second jaw members.

12. The suturing device as recited in claim 11, wherein said first jaw member slides axially across an opening of said recess when the first and second jaw members move between said open orientation and said closed orientation.

13. The suturing device as recited in claim 1, and further comprising a needle push rod disposed proximally of said needle carriage, and being adapted to engage said needle carriage to move said needle carriage proximally and distally.

14. A suturing device for use endoscopically, comprising:
   a first jaw member;
   a second jaw member, said first and second jaw members being disposed at a distal end of said suturing device and being movable between a closed orientation, wherein the first and second jaw members are in close proximity to one another, and an open orientation, wherein the first and second jaw members are substantially spaced from one another;
   a needle carriage which is axially movable between distal and proximal positions at said distal end of said suturing device; and
   at least one needle disposed on said needle carriage, the axial movement of said needle carriage functioning to move said at least one needle between a retracted position and an extended position for passage through tissue grasped between said first and second jaw members.

15. The suturing device as recited in claim 14, and further comprising an actuator disposed at a proximal end of the suturing device, for actuating the first and second jaw members between said closed orientation and said open orientation.

16. The suturing device as recited in claim 15, wherein only one of said first and second jaw members moves when said actuator actuates the jaw members between said closed and said open orientations.

17. The suturing device as recited in claim 15, wherein said actuator comprises a handpiece.

18. The suturing device as recited in claim 17, wherein said handpiece comprises a handle grip and a handle lever, said handle lever being movable relative to said handle grip.

19. The suturing device as recited in claim 18, wherein said handle lever is pivotally movable relative to said handle grip, and is pivotable between a first position corresponding to said closed orientation of said first and second jaw members and a second position corresponding to said open orientation of said first and second jaw members.

20. The suturing device as recited in claim 15, and further comprising a second actuator disposed at the proximal end of said suturing device, for actuating said needle carriage to move axially between said distal and proximal positions.

21. The suturing device as recited in claim 20, wherein said second actuator comprises a knob actuator.

22. The suturing device as recited in claim 14, wherein said at least one needle comprises two spaced needles.

23. A suturing device, comprising:
   a first jaw member;
   a second jaw member, said first and second jaw members being disposed at a distal end of said suturing device, and being movable between a closed orientation, wherein the first and second jaw members are disposed in close proximity to one another, and an open orientation, wherein said first and second jaw, members are substantially spaced from one another;
   at least one needle disposed at the distal end of said suturing device, said at least one needle being movable between a retracted position and an extended position for passage through tissue grasped between said first and second jaw members; and
   a spring for biasing said at least one needle toward said retracted position.

24. The suturing device as recited in claim 23, wherein said at least one needle moves axially between said retracted and extended positions.

25. The suturing device as recited in claim 24, wherein said at least one needle moves distally when moving from said retracted position to said extended position.

26. The suturing device as recited in claim 23, and further comprising apertures in each of said first and second jaw members through which said at least one needle passes when moving between said retracted and extended positions.

27. The suturing device as recited in claim 23, and further comprising at least one can into which said at least one needle is received when said at least one needle moves from said retracted position to said extended position, said at least one can being disposed on an end of a length of suturing material.

28. The suturing device as recited in claim 27, wherein said at least one can is disposed in said second jaw member, which is distal to said first jaw member.

29. The suturing device as recited in claim 27, wherein said at least one can comprises a plurality of tabs for preventing separation of said at least one needle from said at least one can, once said at least one needle has been received by said at least one can.

30. The suturing device as recited in claim 27, wherein the number of needles corresponds to the number of cans.

31. The suturing device as recited in claim 30, wherein there are two needles and two corresponding cans.

32. The suturing device as recited in claim 23, wherein said spring is disposed in a proximal end of said device.

* * * * *